(12) United States Patent
Shakuri-Rad et al.

(10) Patent No.: US 12,064,139 B2
(45) Date of Patent: Aug. 20, 2024

(54) SYSTEM AND METHOD FOR PLACEMENT OF NEUROSTIMULATION LEADS

(71) Applicant: Axonics, Inc., Irvine, CA (US)

(72) Inventors: Jaschar Shakuri-Rad, Morgantown, WV (US); William T. McClellan, Morgantown, WV (US); Justin R. Chambers, Morgantown, WV (US); Zachary Hoopes, Morgantown, WV (US); Guangqiang Jiang, Irvine, CA (US)

(73) Assignee: AXONICS, INC., Irvine, CA (US)

( * ) Notice: Subject to any disclaimer, the term of this patent is extended or adjusted under 35 U.S.C. 154(b) by 0 days.

(21) Appl. No.: 18/135,667

(22) Filed: Apr. 17, 2023

(65) Prior Publication Data

US 2023/0371976 A1 Nov. 23, 2023

Related U.S. Application Data

(60) Provisional application No. 63/411,904, filed on Sep. 30, 2022, provisional application No. 63/331,474, filed on Apr. 15, 2022.

(51) Int. Cl.
*A61B 17/34* (2006.01)
*G16H 30/40* (2018.01)

(52) U.S. Cl.
CPC ......... *A61B 17/3403* (2013.01); *G16H 30/40* (2018.01); *A61B 2017/3407* (2013.01)

(58) Field of Classification Search
CPC ........ A61B 17/3403; A61B 2017/3405; A61B 2017/3407
See application file for complete search history.

(56) References Cited

U.S. PATENT DOCUMENTS

| | | | |
|---|---|---|---|
| 7,715,924 B2 | 5/2010 | Rezai et al. | |
| 8,204,575 B2 | 6/2012 | Stetz et al. | |
| 8,241,301 B2 | 8/2012 | Zhang et al. | |
| 9,439,581 B2 | 9/2016 | Dinsmoor et al. | |
| 9,554,765 B2 | 1/2017 | Godara et al. | |
| 10,092,762 B2 | 10/2018 | Jiang et al. | |
| 10,123,767 B2 * | 11/2018 | Andrews | A61B 8/483 |

(Continued)

FOREIGN PATENT DOCUMENTS

| | | |
|---|---|---|
| CN | 201160895 Y | 12/2008 |
| CN | 207118923 U | 3/2018 |

(Continued)

OTHER PUBLICATIONS

International Search Report and Written Opinion mailed Aug. 7, 2023 by the International Searching Authority in related International Application No. PCT/US2023/018873 filed Apr. 17, 2023.

(Continued)

*Primary Examiner* — Ashley L Fishback
(74) *Attorney, Agent, or Firm* — Gordon Rees Scully & Mansukhani, LLP

(57) ABSTRACT

A system and method for locating and guiding a peripheral nerve evaluation (PNE) lead. The system comprising an X-ray system to capture images of the patient. The images are processed by the system and are provided to a user to utilize a measurement device for inserting a needle for placing leads for the PNE procedure.

21 Claims, 19 Drawing Sheets

(56) References Cited

U.S. PATENT DOCUMENTS

| | | |
|---|---|---|
| 10,327,804 B2 | 6/2019 | Bonde et al. |
| 10,514,243 B2 | 12/2019 | Gjertsen |
| 10,716,593 B2 | 7/2020 | Chiegn |
| 11,020,201 B2 * | 6/2021 | Vogele ............ A61B 17/00234 |
| 11,109,821 B2 | 9/2021 | Crites-Bachert |
| 11,241,573 B2 | 2/2022 | John et al. |
| 11,382,655 B2 | 7/2022 | Bouazza-Marouf et al. |
| 2003/0199785 A1 * | 10/2003 | Hibner ............... A61B 17/3403 |
| | | 600/562 |
| 2008/0039866 A1 | 2/2008 | Stetz et al. |
| 2008/0140082 A1 | 6/2008 | Erdem et al. |
| 2010/0114100 A1 | 5/2010 | Mehdizade |
| 2012/0172700 A1 | 7/2012 | Krishnan et al. |
| 2017/0311978 A1 | 11/2017 | Chieng |
| 2019/0216569 A1 | 7/2019 | Al-Shawi et al. |
| 2021/0015448 A1 | 1/2021 | Sokulin et al. |
| 2021/0045711 A1 | 2/2021 | Brattain et al. |
| 2021/0128926 A1 | 5/2021 | Crites-Bachert |

FOREIGN PATENT DOCUMENTS

| | | |
|---|---|---|
| CN | 111821000 A | 10/2020 |
| WO | 2022187144 A1 | 9/2022 |

OTHER PUBLICATIONS

International Search Report and Written Opinion mailed Aug. 15, 2023 by the International Searching Authority in related International Application No. PCT/US2023/017295 filed Apr. 3, 2023.

Michael P. Feloney et al.; "Sacral Neuromodulation"; http://www.ncbi.nlm.nih.gov/books/NBK567751/; NCBI Bookshelf; National Library of Medicine; National Institutes of Health; Jan. 2023.

* cited by examiner

SYSTEM AND METHOD FOR PLACEMENT OF NEUROSTIMULATION LEADS

CROSS-REFERENCE TO RELATED PATENT APPLICATIONS

This application claims priority to and the benefit of U.S. Provisional Patent Application No. 63/411,904 filed Sep. 30, 2022, and U.S. Provisional Patent Application No. 63/331,474 filed Apr. 15, 2022, both of which are incorporated by reference herein in their entireties.

GENERAL DESCRIPTION

This application relates to devices and methods to assist with the placement of leads used in neurostimulation. In the exemplary embodiment, the device and method relate to the placement of an electrical lead used in sacral neuromodulation, and more particularly, to a device and method for locating the sacral foramina during a peripheral nerve evaluation (PNE) procedure in order to place the electrical leads of a PNE system in the appropriate position.

Sacral neuromodulation is a treatment for bladder and bowel dysfunction, which involves implanting a device that provides controlled electrical stimulation to the sacral S3 spinal nerve in the patient. Prior to receiving a permanent implant, the patient undergoes a procedure called a peripheral nerve evaluation (PNE). The procedure involves implanting temporary leads into the patient with the leads connected to an external pulse generator, and then observing results for a period of time, usually anywhere between 3 to 14 days. If the results meet certain clinical standards, then the patient may be a candidate for receiving an implantable pulse generator for sacral neuromodulation.

Current techniques for lead placement during the evaluation procedure involve identifying palpable skeletal or bony landmarks on the patient and inserting a foramen needle into the patient based on the location of these landmarks. The objective during this procedure is to insert the foramen needle through the skin and into the S3 foramen such that an electrical stimulation lead may be provided along the sacral S3 spinal nerve. The procedure may be performed in an operating room setting with fluoroscopic or other image guidance to provide for more accurate placement of the leads. However, this procedure is most often performed in an office setting under local anesthesia and without imaging. In an office setting, the placement method is essentially a "blind" insertion method because it does not rely on a picture or fluoroscopy of the patient's anatomy.

When fluoroscopy or other imaging is not used, such as in the office setting, the physician inserts the foramen needle from outside the patient's body and into the S3 foramen based on experience and by referencing the palpable landmarks. The physician cannot see the S3 foramen when they are attempting to place the foramen needle through the S3 foramen. The use of palpable skeletal or bony landmarks is based on normal anatomy without consideration for anatomic or pathologic variations. This may lead to improper placement of leads in an office setting and eventual failure of the PNE. For example, it is often the case that plural attempts are required to locate the S3 foramen and successfully insert the foramen needle through it. In some instances, due to multiple failed attempts at proper needle placement, a patient may even abandon the PNE (and thus sacral neuromodulation altogether) without ever having the leads properly placed. Misplaced leads may also lead to a less than ideal clinical outcome and a premature abandonment of an otherwise efficacious treatment. Thus, there remains a demand and need to provide an improved system and method for PNE lead placement

SUMMARY

The embodiments disclosed herein relate to devices and methods that improve efficacy and efficiency of locating the sacral foramina during a sacral neuromodulation procedure. Embodiments include imaging a portion of the patient, identifying internal points of the patient in the imaging, calculating measurements based on the imaging and the identified points, transferring the measurements to a device, placing the device on and exterior to the patient using a locating feature, and guiding a medical element (e.g., a foramen needle) into the patient using an element guide of the device. The disclosed embodiments help the physician more accurately locate the S3 foramen and provide an improvement over conventional techniques that are less accurate at locating the S3 foramen during a blind insertion.

According to one embodiment disclosed herein a method includes the steps of: determining one or more measurements from at least one image of a sacrum of a patient; applying the determined one or more measurements with a guide device; locating the guide device on the patient's backside using a landmark; and while the guide device is located on the patient's backside, using the guide device to guide insertion of a medical element into the patient.

According to another disclosed embodiment a device for guiding medical element insertion includes: an elongated base with a locating feature that references a landmark on a patient; a head that is translatable along the elongated base in a first direction; a medical element guide that is translatable along the head in a second direction perpendicular to the first direction, wherein the medical element guide is configured to identify the entry location and angle of insertion of a medical element into the patient.

In yet another disclosed embodiment, a system and method is disclosed that includes one or more computer readable storage media having program instructions collectively stored on the one or more computer readable storage media or remote cloud based services. The program instructions are executable to: receive at least one image of a sacrum of a patient; display image; receive user input defining points of interest in the displayed image; determine one or more measurements for a medical element guide based on the points of interest and a predefined dimension of the medical element guide; and output the determined one or more measurements to a user.

DETAILED DESCRIPTION

The particulars shown herein are by way of example and for purposes of illustrative discussion of the disclosed embodiments and are presented to provide a readily understood description of the principles and conceptual aspects. In this regard, no attempt is made to show structural details in more detail than is necessary for a fundamental understanding, and the description taken together with the drawings make apparent to those skilled in the art how the disclosed devices and methods may be embodied in practice.

Figure 1:
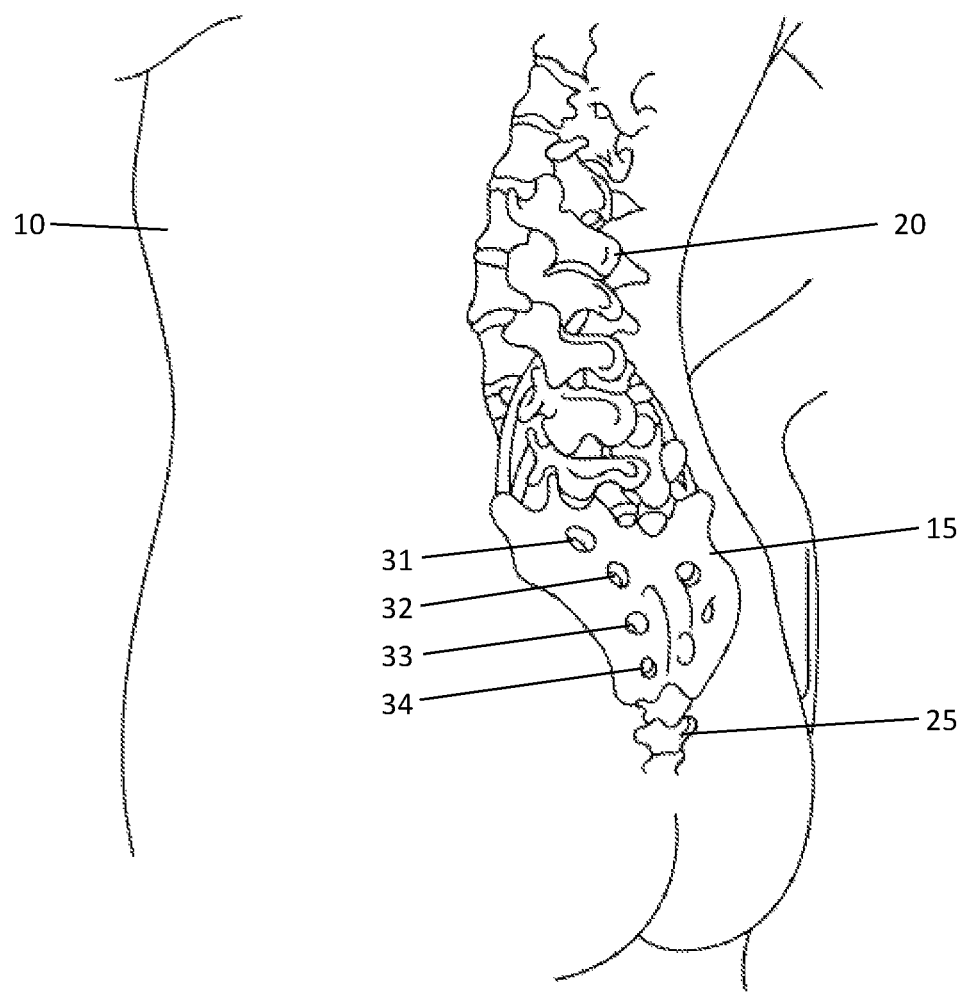
FIG. 1 shows an exemplary partial view of the human anatomy.

FIG. 1 shows an exemplary partial view of certain skeletal components of a human torso 10 including the sacrum 15 at the base of the spine 20, and the coccyx 25 at the base of the sacrum 15. As shown in FIG. 1, the sacrum 15 includes two groups of sacral foramina, or openings through which the sacral nerves pass, arranged in two vertical rows, each respectively located on either side of the medial sacral crest. In FIG. 1, foramen 31 corresponds to the S1 foramen, foramen 32 corresponds to the S2 foramen, foramen 33 corresponds to the S3 foramen, and foramen 34 corresponds to the S4 foramen. Only one group of sacral foramina is shown and numbered in FIG. 1. A system and method for accurately locating a selected one of the foramina 31-34 and inserting a needle through the selected one of the foramina to access a nerve for implanting a component of a sacral neuromodulation system is disclosed herein. Embodiments are described herein with respect to locating and inserting a foramen needle through the S3 foramen; however, the described system and method is not limited to use with the S3 foramen.

Figure 2:
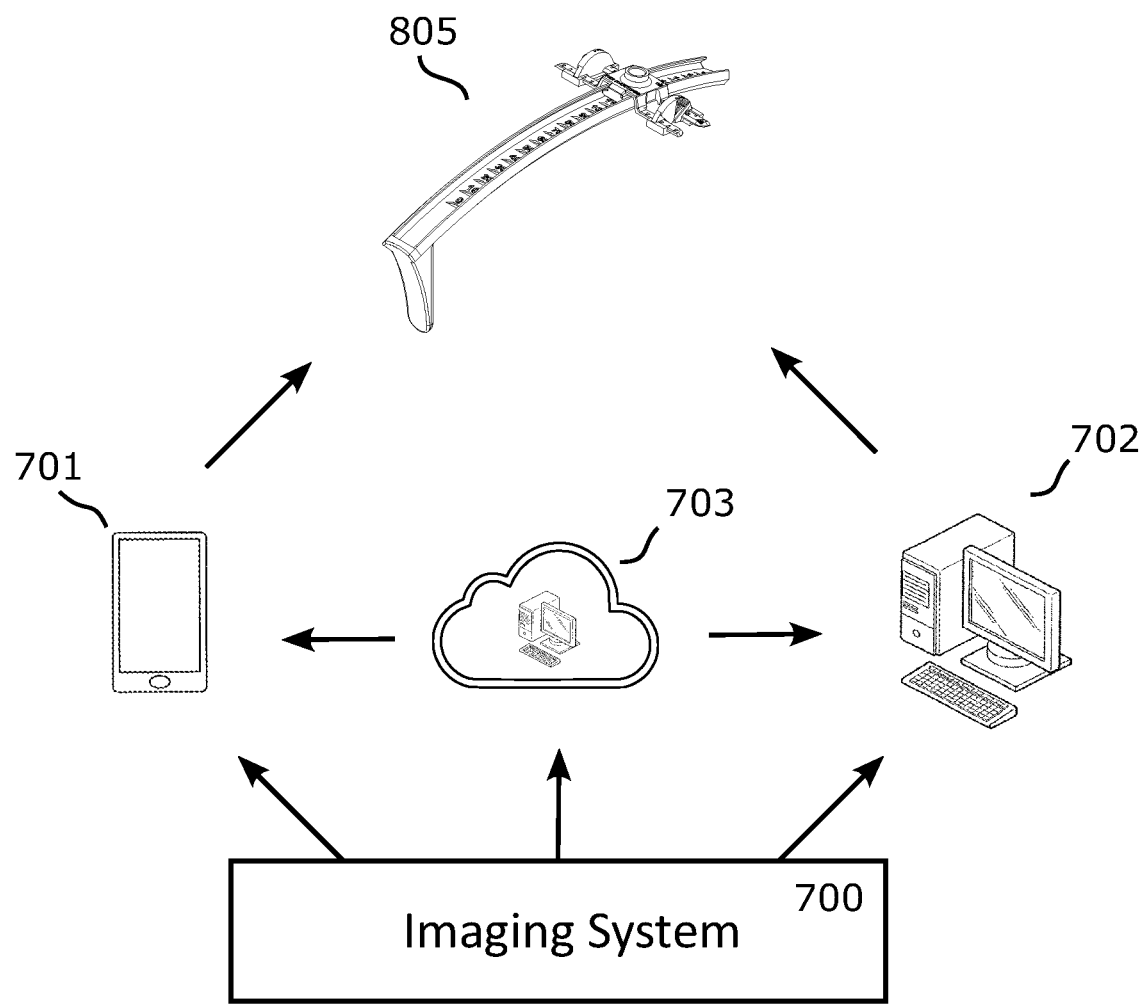
FIG. 2 shows the elements of an exemplary medical element locating and placement system.

FIG. 2. shows the components of medical element placement system 100 which includes an imaging system 700 that may communicate with one or more electronic devices. Although X-ray or fluoroscopic imaging is preferred, other imaging technologies that show and distinguish internal bone structure of the patient may be used. The electronic device may include a smartphone or other mobile device 701, a computer 702, or any other known electronic device that is capable of receiving inputs from the imaging system 700 and displaying outputs on the display of the electronic device. In addition to (or as an alternative to) the display, the electronic device may provide various indications to the user through audible or visual alerts or messaging. The imaging system 700 is configured to capture images of a patient requiring a PNE procedure. The medical element placement system 100 requires images to be taken in both the anterior-posterior (or posterior-anterior) and lateral planes in order to provide the measurements required to place the PNE lead in the correct location. Once the images have been captured, images from the imaging system 700 may be sent to the electronic device(s) which is configured to run or function with an application (e.g., software) that is configured to process the images and provide information that may be used to properly position a needle guide device 805 on the patient and mark the patient as necessary to identify the insertion point for a foramen needle used for placement of the PNE lead.

In one embodiment, the application may run using a cloud-based computing service 703 that communicates with the electronic device. The cloud-based computing service may perform the calculations required to identify a preferred point of needle entry (and angle) and provide the resulting location and angle the electronic device. The electronic device may run the application (or a web client that accesses a cloud-run version of the application) described below with respect to FIGS. 6 and 7, and the application may provide various information on the display (e.g., screen) on the screen of the electronic device. For example, the electronic device may display the coordinates (e.g., markings on the needle guide device 805) and angle to be used for needle insertion on the patient. The information provided by the application can then be applied to the needle guide device 805 to aid in the placement and insertion of a needle onto the patient.

The program may also incorporate the use of machine learning or artificial intelligence (AI) in order to provide enhanced image recognition capabilities. The image recognition capability or feature may allow the program or application to automatically provide the points of interest, draw or impose the required lines on the image, and calculate measurements based on the images provided to the program. The image recognition feature may also provide the points of interest regardless of the orientation of the patient during the imaging. Thus, if the patient appears in an inconsistent position with regard to the axis of the image, the measurements may still be obtained due to the ability of the employed AI to recognize the anatomical points of interest. As mentioned above, the "drawing" of lines may be visible to the user of the program or merely performed inherently as part of the operation of the program or application that determines or calculates the required measurements and the preferred location for needle insertion.

Figure 3:
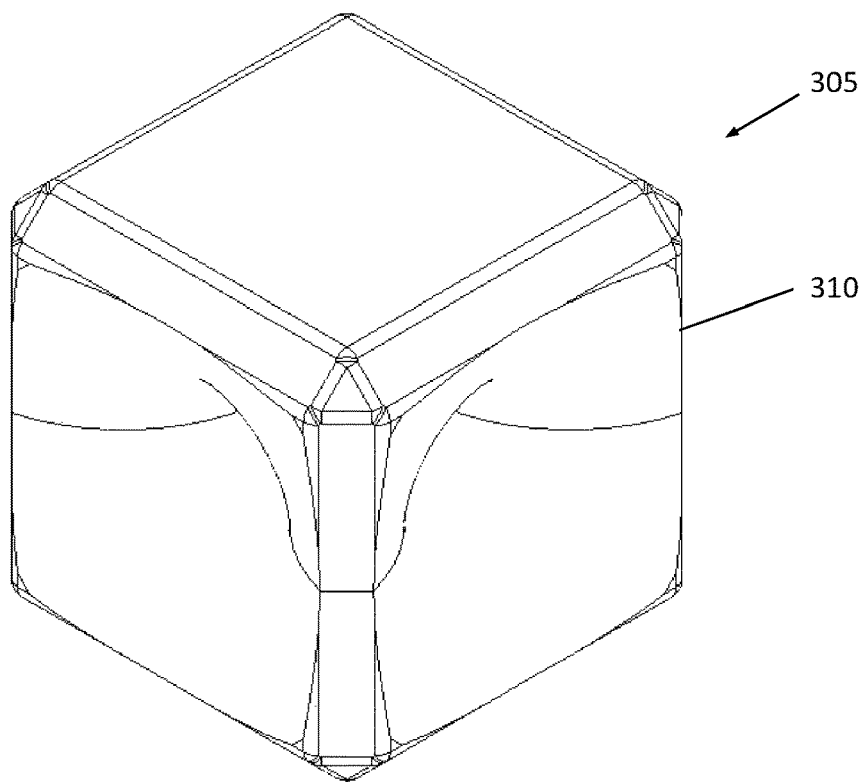
FIG. 3 shows an example of a radiopaque landmark device.
Figure 4:
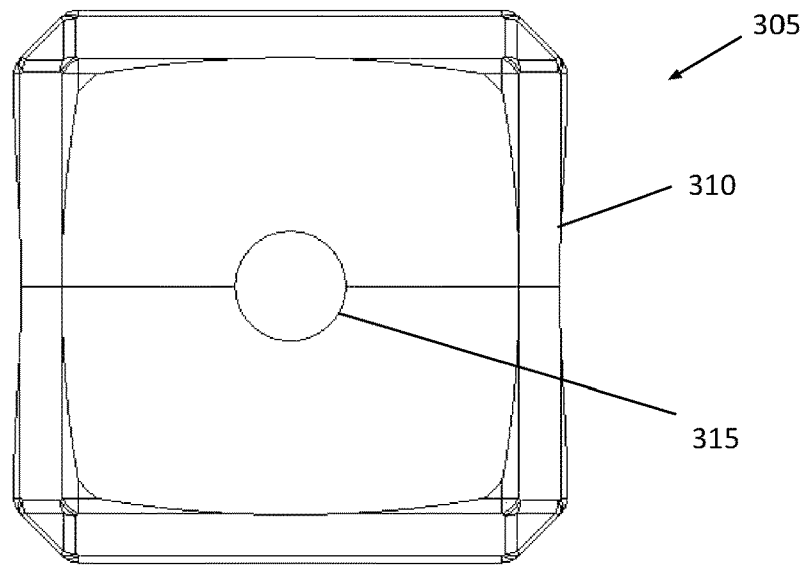
FIG. 4 shows an example of a radiopaque landmark device.

FIGS. 3 and 4 show an example of a radiopaque landmark device 305 that may be used with the imaging of the patient. The imaging includes an X-ray of the lateral plane of the patient showing both the sacrum 15 and coccyx 25 of the patient. The imaging may also include one or both of the anterior-posterior (AP) or posterior-anterior (PA) planes of the same area (i.e., showing the sacrum and coccyx of the patient). The radiopaque landmark device 305 may be placed on the patient during the X-ray imaging in the field of view of the imaging device 700. The radiopaque landmark device 305 includes a radio-transparent housing 310 and a radiopaque element 315. The radio-transparent housing 310 is composed of a material that is relatively transparent to an X-ray device (or whatever imaging technology is used). Plastic may be used for the radio-transparent housing 310, for example. The radio-transparent housing 310 provides for easy placement handling of the radiopaque landmark device 305 onto the patient when images are being taken. The radiopaque element 315 is composed of a material that is relatively opaque to an X-ray (or whatever imaging technology is used). Stainless steel may be used for the radiopaque element 315, for example. The radiopaque element 315 has a predefined dimension that is used with the X-ray image(s) to define a scale of the image(s) of the patient and provide a reference to properly determine the measurements required to locate the insertion point for a needle on a patient. In a particular embodiment, the radiopaque element 315 includes a sphere of a predefined diameter so that the radiopaque landmark device 305 may be placed in any orientation on the patient during the imaging. Many other known landmark devices may be utilized, such as radiopaque devices with different predetermined shapes and dimensions. Landmark devices may be fixed onto the patient or the radiographic table where X-ray image is taken.

Figure 5:
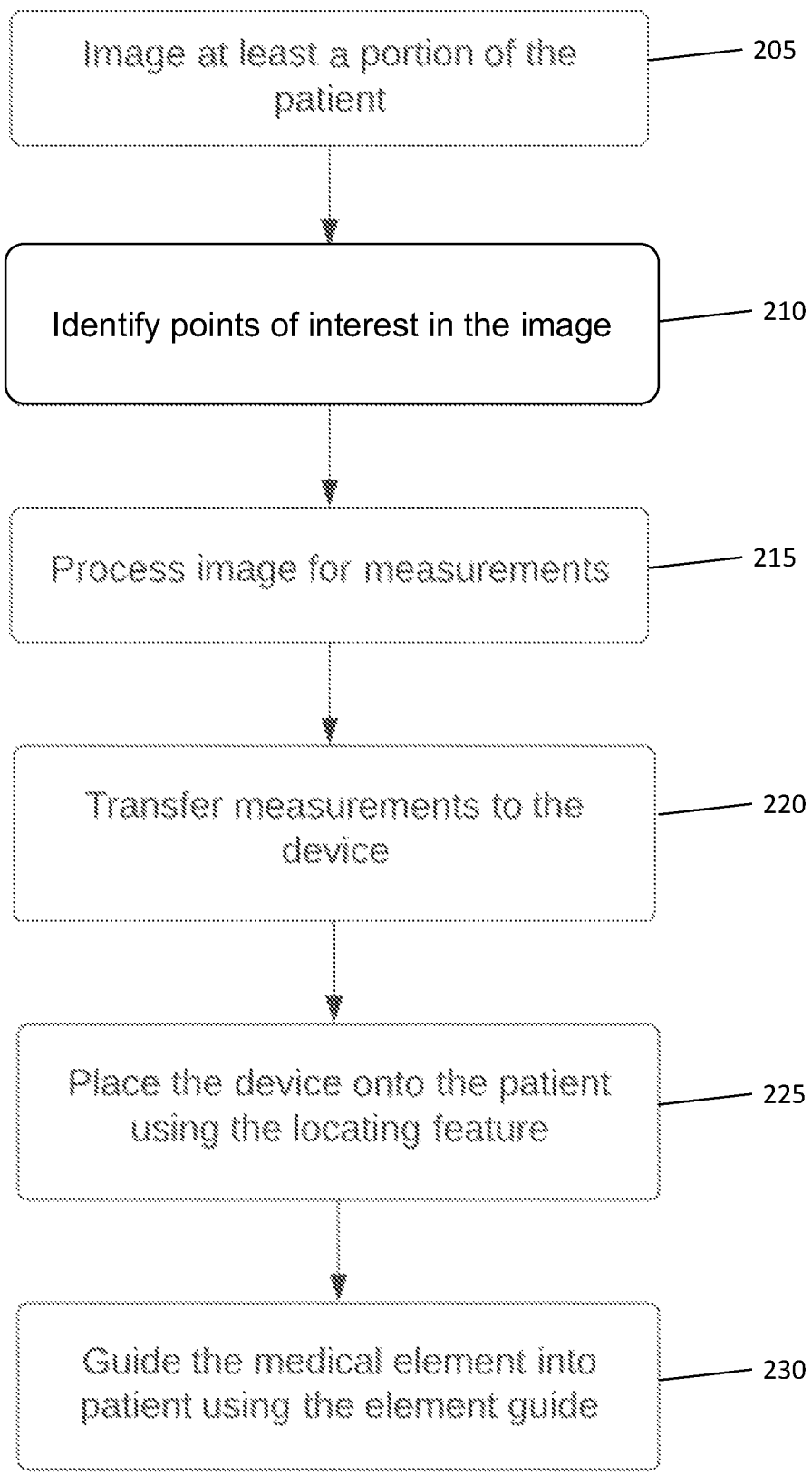
FIG. 5 shows a flowchart of an exemplary method of locating an insertion point and placement of a medical element.

FIG. 5 shows a flowchart of an exemplary method. Step 205 includes imaging a portion of the patient. The images of the patient may be obtained with the patient in various positions. The imaging system 700 may capture images of the patient's sacrum 15 and coccyx 25 in both the anterior-posterior (or posterior anterior) and the lateral planes. The processing software of the imaging system 700 may set the appropriate dimensions using a scale provided by a radiopaque landmark device or by the imaging system 700. The processing software of the imaging system 700 may automatically manipulate the image further in order to clarify the image (e.g. modifying contrast or brightness of the image). The image may also be further clarified once transferred to the electronic device.

Step 210 includes identifying internal points of interest related to the patient in the imaging to determine key measurements used in the calculation. Step 215 includes calculating measurements that identify the recommended insertion location of the needle based on the imaging and the identified points. These measurements may be used to position elements of the needle guide device 805. The software may also calculate the needle entry angle α and the minimum needle length. The minimum needle length is defined as the minimum needle length that is required to reach the target location (e.g., the S3 sacral foramen).

Step 220 includes transferring the measurements calculated in Step 215 to the needle guide device 805. Step 225 includes placing the needle guide device 805 on and exterior to the patient using a locating feature. Step 230 includes guiding a medical element (e.g., a foramen needle) into the patient using an element guide of the device 805. Embodiments implementing these steps will become apparent from the following figures and associated descriptions.

Figure 6:
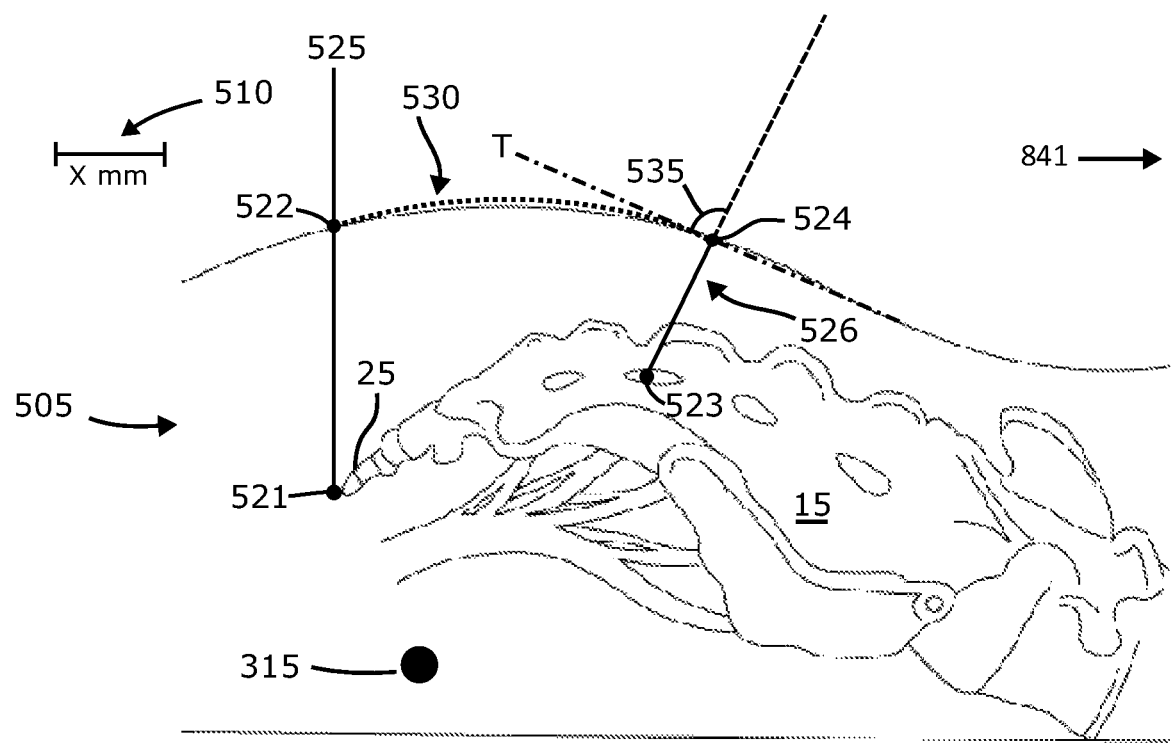
FIGS. 6 and 7 show exemplary implementations of identifying points in a fluoroscopic image and processing the image for measurements.
Figure 7:
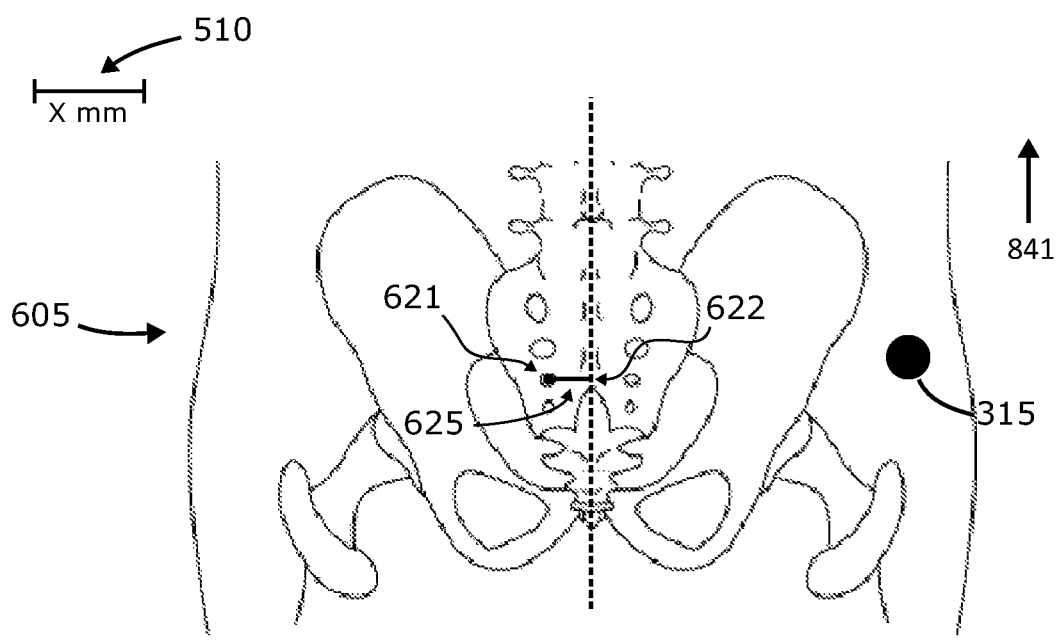

FIGS. 6 and 7 show shows an exemplary X-ray image 505 in which the radiopaque element 315 of the radiopaque landmark device 305 is visible. Because the radiopaque element 315 has a predefined diameter, this known measurement of the radiopaque element 315 may be used to define a scale for the X-ray image 505. This scale may be used by the application when calculating measurements as described herein. A scale indicator 510 (e.g., a scale line embedded and depicted on an x-ray image) may also be provided as an alternative to the landmark device 305, when the imaging system 700 is capable of including an automatic scaling function that provides a scale of the image. The scale indicator 510 may adjust to correspond to the selected image magnification by a user. In both alternatives (e.g., using the radiopaque landmark device 305 or the automatic scaling function), the image is provided with a scale of the image that may be used when calculating the measurements necessary to identify the location for needle insertion required for proper lead placement. When an image scale 510 cannot be provided by the imaging system 700, it is essential that the radiopaque landmark is used so that the image can still be properly measured.

FIGS. 6 and 7 also show exemplary implementations of identifying points in the image(s) and processing the image(s) for measurements that may be used at steps 210 and 215, respectively. The measurements refer to the coordinates or location of the needle insertion point on the patient. As mentioned above, these measurements can be transferred to the needle guide device 805. The image(s) from step 205 are uploaded to an electronic device (not shown) for processing. The electronic device may be, for example, a desktop computer, laptop computer, tablet computer, or a smartphone that runs a specialized software (e.g., a proprietary application). The application may be part of a software program product as described herein. Alternatively, all or part of the processing may be conducted in a cloud-based application.

The electronic device may include a display for displaying images (e.g., X-rays taken at step 205) and a user input mechanism that permits the user to identify points in a displayed image. The display and user input mechanism may be combined in a touchscreen display, for example, that can display an image and receive user touch input defining points of interest in the image. The display and user input mechanism may be separate, for example, such as a display screen that displays an image and a mouse or trackball that controls a pointer (e.g., cursor, arrow, etc.) superimposed on the displayed image, and a button the user may depress to provide define a current location of the pointer on the image as a point of interest in the image.

The step of identifying points in the image in step 210 includes importing the one or more images from step 205 into the application running on the electronic device. The application establishes a scale of the image(s) using either the predefined dimension of the radiopaque element 315 in the image(s) or a scale indicator (e.g., such as scale indicator 510) provided with the image(s). Step 210 may optionally include the application adjusting visual aspects of the image(s), such as contrast, etc. FIG. 6 shows an example of a simplified lateral X-ray image 505 that includes a scale indicator 510 that defines a scale of the image 505.

With continued reference to FIG. 6, the application receives user input via the electronic device. The user uses the image to identify the points of interest in the image 505. The user may interact with the image (e.g., via a touch screen, keyboard, stencil, etc.) to identify the points of image. There are four points of interest 521, 522, 523, and 524 that are defined by user input. The application may provide one or more messages to the user that prompt the user to provide their input for one or more of the points of interest. The user provides input to define the first point of interest 521 at the tip (e.g., distal end) of the coccyx in the image 505. In response to receiving this input, the application draws a vertical line 525 upward from the first point of interest 521. While the line 525 is displayed, the user provides input to define the second point of interest 522 at the intersection of the line 525 and the outer surface of the skin of the patient. The user provides input to define the third point of interest 523 at the center of the targeted foramen, in this case the S3 sacral foramen, in the image 505. In response to receiving this input, the application draws a line 526 perpendicular to the sacrum at third point of interest 523 and upward toward the outer surface of the skin of the patient. While the line 526 is displayed, the user provides input to adjust or confirm that the line 526 is perpendicular to the sacrum and provides input to define the fourth point of interest 524 at the intersection of the line 526 and the outer surface of the skin of the patient.

In the event that the images are not fully legible (i.e., S3 not fully visible) the application may suggest where to target the S3 foramen based on other points of interest. For example, as an alternative to asking for point of interest 523, the program may ask locations of the lumbosacral joint (the junction of L5 vertebrae and S1) and the caudal tip of the coccyx 521. The program may then estimate the location of 523 by calculating a point halfway between the lumbosacral joint and the caudal tip of the coccyx 521. Other alternatives may include providing estimations of where the S3 foramen is located by providing known measurements of the average location of the S3 foramen of the human anatomy (e.g., S3 is approximately 11 cm from the tip of the coccyx).

The method described herein may include utilizing image processing software. For example, the application interacting with the electronic device may include image processing software to facilitate processing the image. The image processing software may provide the user with the ability to utilize the following functions with regard to the image: pan, zoom, windowing, scroll, crosshair, filtering (brightness and contrast adjustment), measurement of distance, angles and areas, image rotation/flip, etc. The aforementioned image processing capabilities may run in the background of the application and software without user input, or may be provided as options for the user to manipulate the image in order to assist with the identification of points of interest.

The image processing software may be specialized for handling the image files typically associated with fluoroscopy images (e.g., DICOM files). Digital Imaging and Communications in Medicine (DICOM) is the international standard for medical images and related information. DICOM defines the formats for medical images that can be exchanged with the data and quality necessary for clinical use. The processing software may provide the ability to create a 3D reconstruction model of the patient and the patient's skeletal structure in order to assist in the location of the sacral foramen and preferred needle entry point. In addition, the image processing software may be configured to anonymize and de-identify any patient details retained in the image so that the image can be employed in machine learning and AI applications.

Processing the image for measurements at step 215 includes determining a length measurement, an angle measurement, and a depth measurement based on the points of interest defined by the user at step 210. The application determines the length measurement, the angle measurement, and the depth measurement based on: the coordinates (e.g., X-Y cartesian coordinates) of each of the points of interest in a coordinate system defined for the image; the scale of the image relative to the same coordinate system; and one or more predefined dimensions of a device that will be utilized as a needle guide using the determined length measurement and angle measurement. The one or more predefined dimensions of the device include a predefined radius of curvature of an elongated base of the device. The application uses this information (e.g., the coordinates, the scale, and the predefined dimensions of the device) as inputs to an algorithm or program that employs established geometric and trigonometric formulas and calculations to determine: (i) a length of an arc 530 that extends between the second point 522 and the fourth point 524 where the arc has the predefined radius of curvature; (ii) an angle 535 between the line 526 and a tangent of the arc 530 at the fourth point 524; and (iii) a length of the line 526 between the third point 523 and the fourth point 524. The determined length of the arc 530 between the second point 522 and the fourth point 524 includes the length measurement, the determined angle 535 includes the angle measurement, and the determined length of the line 526 between the third point 523 and the fourth point 524 includes the depth measurement. The application outputs the determined measurements to the user, e.g., via a display. The angle 535 may be calculated as the angle between an extension of the line 526 and a tangent line "T" that is tangent to the arc 530 at point 524.

FIG. 7 shows an example of a posterior-anterior (PA) X-ray image 605. The application receives user input via the computing device when the user identifies points of interest in the image 605. The user may interact with the image (e.g., via a touch screen, keyboard, stencil, etc.) to identify the supplemental points of interest 621, 622 on the image. The first supplemental point of interest 621 is located at the center of the S3 foramen in the image 505. In response to receiving this input from the user, the application draws a line 625 that intersects the point 621 and is perpendicular to the centerline of the sacrum. While the line 625 is displayed, the user identifies the second supplementary point of interest 622 at the intersection of the line 625 and the centerline of the sacrum. In this example, the application uses the coordinates of the points 621 and 622 to determine a lateral distance between the points 621 and 622. The application outputs the determined measurement to the user, e.g., via a display. The user may edit any one or more of the points of interest (i.e., 521, 522, 523, 524, 621, 622) and the program may automatically recalculate the measurements outputted based on the updated point(s) automatically. The step of identifying the supplementary points of interest may be omitted, and the application can assume a standard distance in the range of about 20 to 25 mm, based on published research or studies.

Figure 8A:
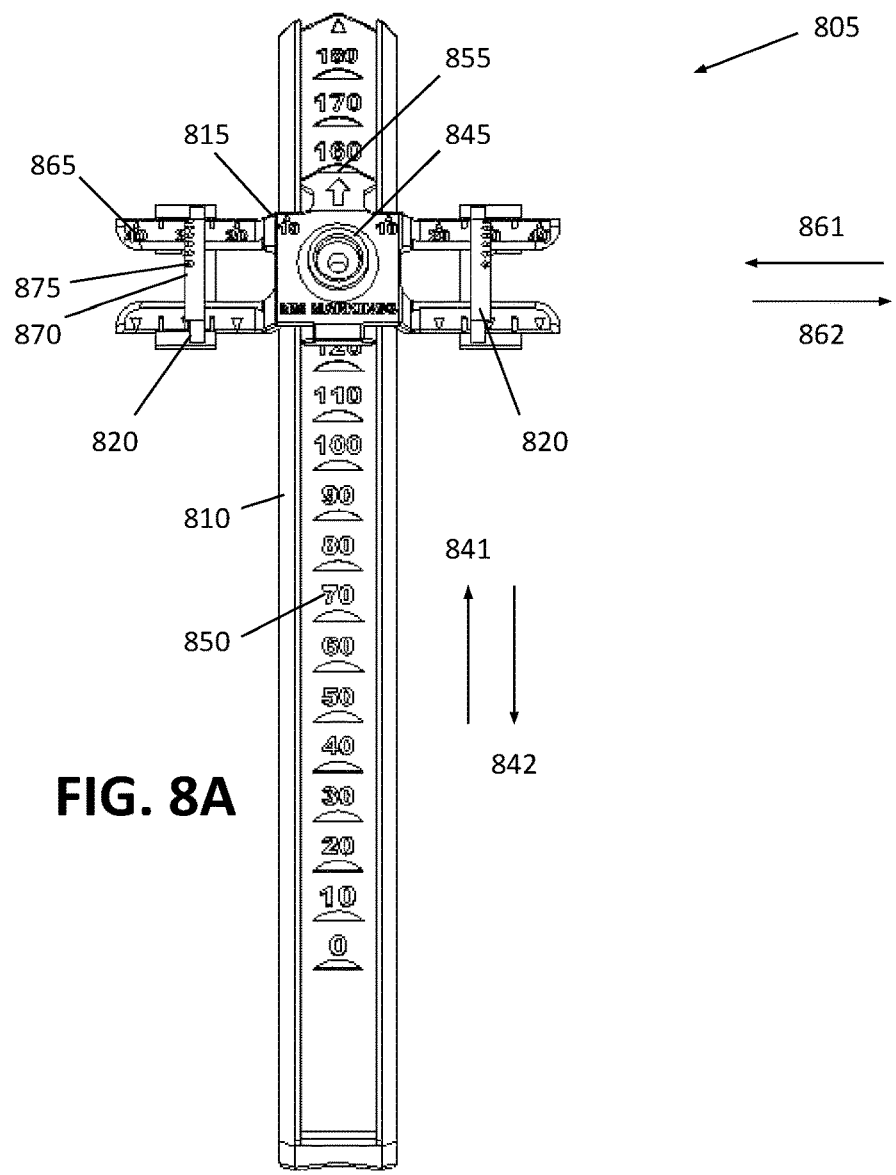
FIGS. 8A-G show an exemplary needle guide device.
Figure 8B:
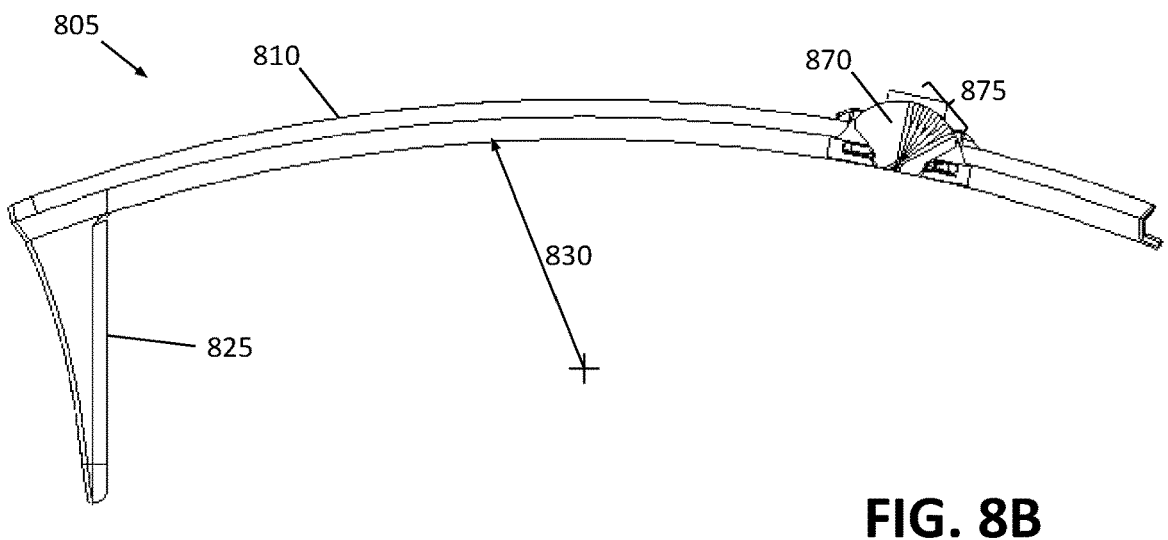
Figure 8C:
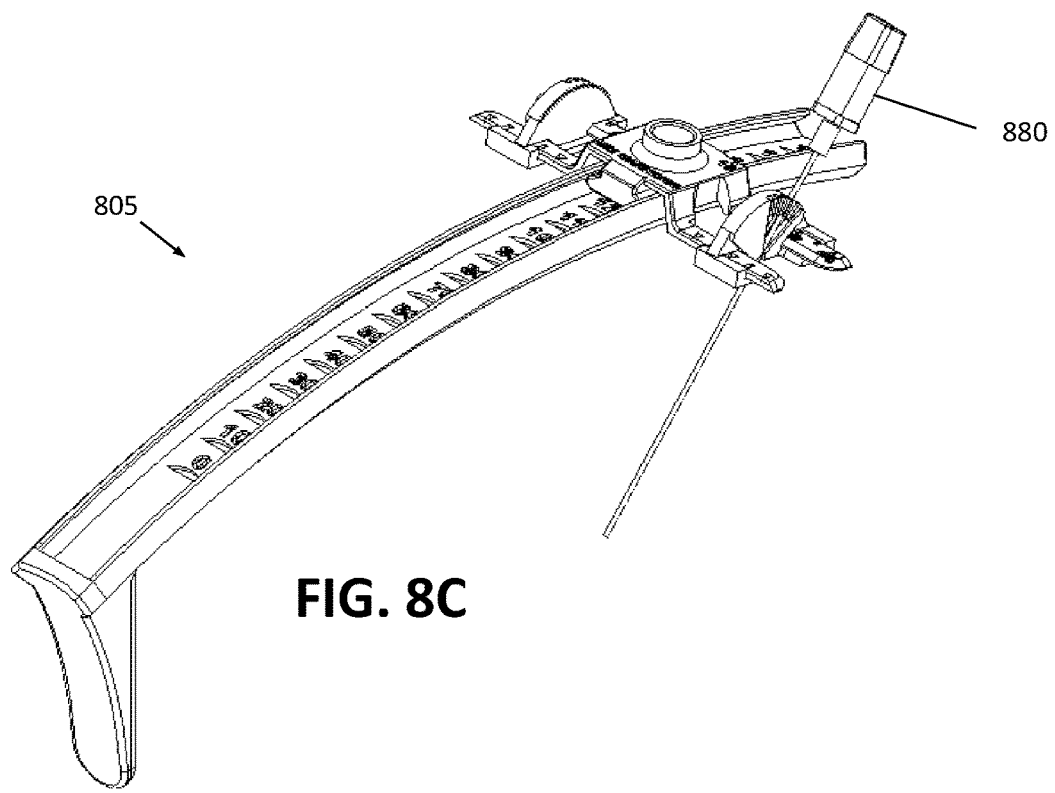
Figure 8D:
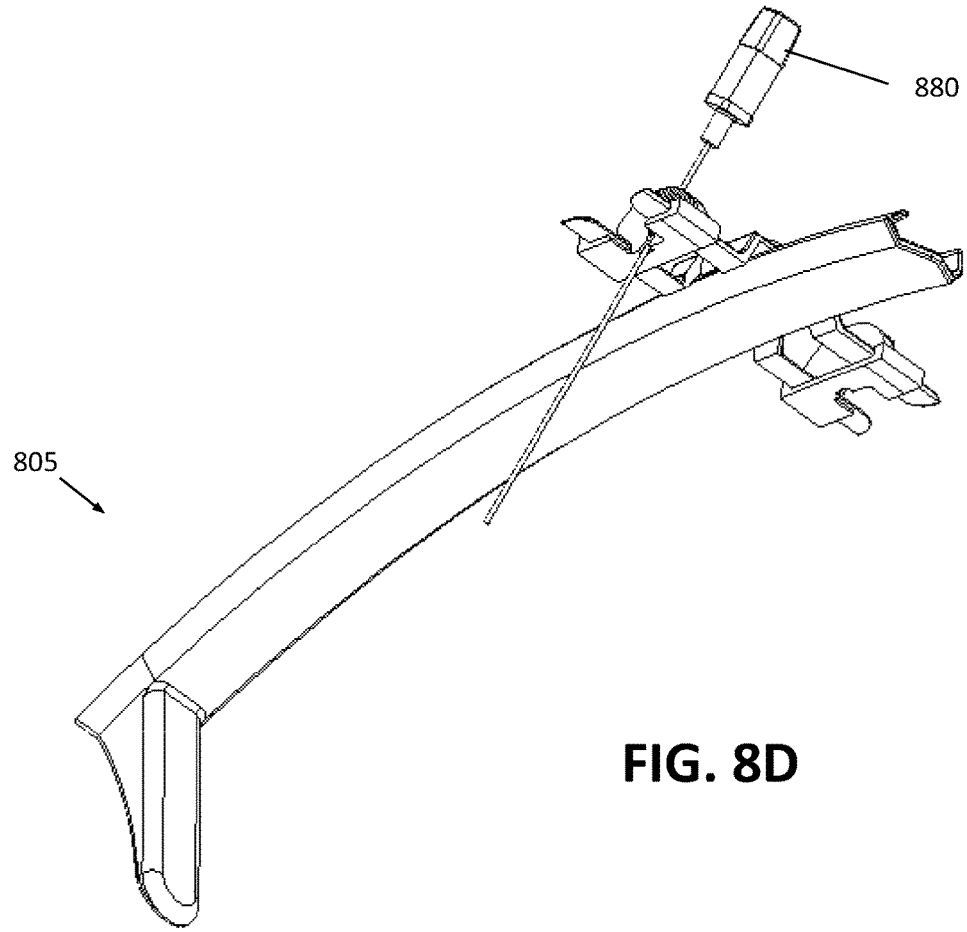
Figure 8E:
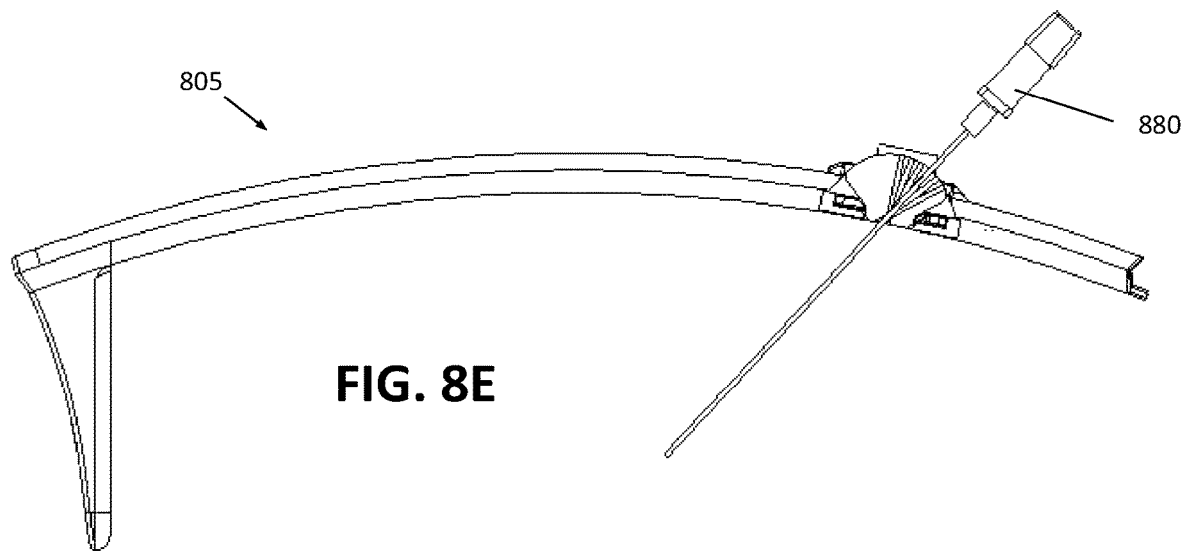
Figure 8F:
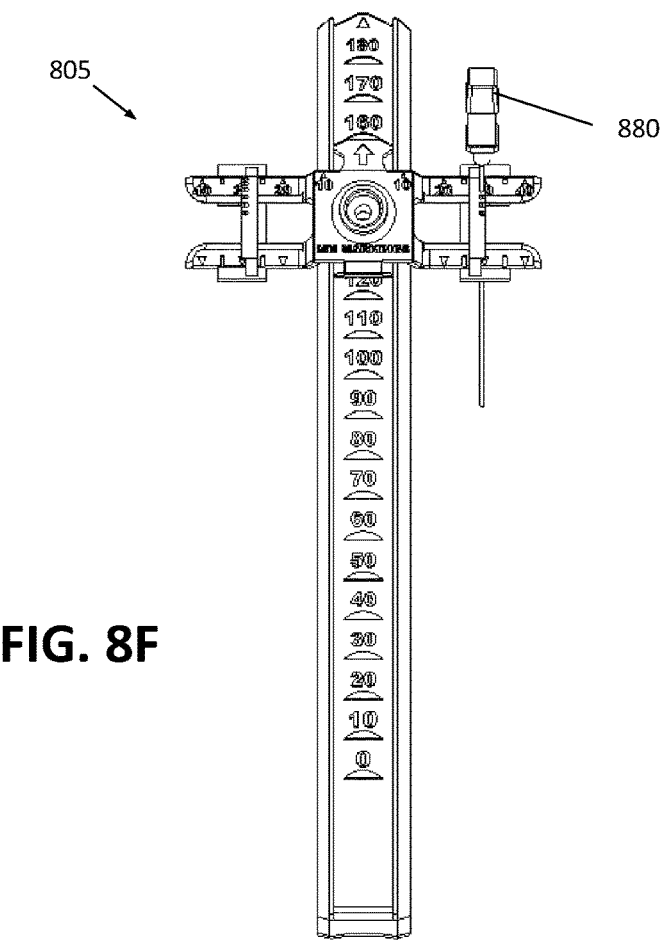

FIGS. 8A and 8B show an exemplary needle guide device 805. The device 805 includes an elongated base 810, a sliding lateral member 815, and medical element guides 820. The device 805 includes a depending portion 825 that extends downward from a bottom surface of the elongated base 810. The bottom surface of the elongated base 810 has a radius of curvature 830 that is one of the one or more predefined dimension of the device described with respect to FIG. 6 and used in the application to determine measurements. In another embodiment, the elongated base 810 may not be entirely curved or arc shaped. Instead, the elongated base 810 may include a flat portion which better conforms to the topographical shape of the patient. In one embodiment, the optional flat portion is located at the end of the elongated base 810 positioned closer to the head of the patient. The sliding lateral member 815 may also slide along this flat portion.

The elongated base 810 may include a coccyx locating feature (e.g., the depending portion 825) that is used to locate the device 805 on to the patient. The coccyx locating feature is pressed against the coccyx while the arced feature is located along the midline defined by the sagittal plane of the patient. The arced feature of the elongated base 810 is a predefined arc geometry that is used by the application for determining measurements at step 215. The sliding lateral member 815 slides along the elongated base 810 and remains square to the elongated base 810. The sliding lateral member 815 may be locked at a specific location along the elongated base 810. The elongated base 810 has measurements included to set the sliding lateral member 815 at the location determined by the calculations and measurements from patient imaging. The sliding lateral member 815 includes lateral rails that allow for the use of the medical element guide 820. The medical element guide 820 slides laterally along the sliding lateral member 815 and remains square to the sliding lateral member 815. The lateral placement may be set based on imaging measurements or standard practices. The medical element guide 820 allows for needle placement at various degrees. The medical element guide 820 allows the user to fix the needle at a defined angle in use. The medical element guide 820 and the sliding lateral member 815 are also designed to allow removal of the device 805 while a needle remains with the patient. The marks on the needle are also used to measure the depth of the needle placement. This measurement is generated during image measurements and may be used to located depth of the foramen needle in the patient.

The sliding lateral member 815 may be moved translationally relative to the elongated base 810 in a first direction 841 (i.e., cephalad direction) and a second direction 842 (i.e., caudad direction) opposite the first direction along a length of the elongated base 810. The sliding lateral member 815 includes a locking mechanism 845 that permits a user to selectively lock (e.g., prevent) and unlock (e.g., permit) the translational movement of the sliding lateral member 815 relative to the elongated base 810. The locking mechanism may include a thumb screw or other conventional or later developed locking mechanism that may be used to selectively lock (e.g., prevent) and unlock (e.g., permit) the translational movement of one device sliding along another device. The elongated base 810 may include indicia 850 that correspond to units of the length measurement determined at step 215. In the example shown in FIG. 8A, the indicia 850 include a scale of millimeters from 0 to 180 along the length of the elongated base 810.

With continued reference to FIG. 8A, the step of transferring the measurements to the device 220 includes moving the sliding lateral member 815 to a position on the elongated base 810 such that an indicator 855 of the sliding lateral member coincides with a location in the scale of the indicia 850 that matches the length measurement determined at step 215. In the example of FIG. 6, the length measurement is determined to be 136.8 mm. Using this exemplary length measurement, at step 220 the user would move the sliding lateral member 815 along the elongated base 810 until the indicator 855 coincides with a location corresponding to the number 136.8 on the scale of the indicia 850. In situations where the number of the length measurement does not align exactly with one of the numbers of the indicia 850, the user may interpolate a position for the indicator 855 between two numbers of the indicia 850 that best matches the length measurement. After positioning the sliding lateral member 815 on the elongated base 810 according to the length measurement, the user locks the sliding lateral member 815 relative to the elongated base 810 using the locking mechanism 845.

In the example shown in FIG. 8A, the device 805 includes medical element guides 820 that may be moved translationally relative to the sliding lateral member 815 in a first direction 861 and a second direction 862 opposite the first direction, where the direction of translation of the medical element guides 820 relative to the sliding lateral member 815 is perpendicular to the direction of translation of the sliding lateral member 815 relative to the elongated base 810. The device 805 includes respective locking mechanisms that permit a user to selectively lock (e.g., prevent) and unlock (e.g., permit) the translational movement of each medical element guide 820 relative to the sliding lateral member 815. The locking mechanism may include a thumb screw or other conventional or later developed locking mechanism that may be used to selectively lock (e.g., prevent) and unlock (e.g., permit) the translational movement of one device sliding along another device. Alternative to locking mechanisms, the sliding lateral member 815 and/or the medical element guides 820 may include detents that define predefined locations of the medical element guides 820 on the sliding lateral member 815.

Each wing of the sliding lateral member 815 may include indicia 865 that correspond to units of the lateral distance determined at step 215 (e.g., as described at FIG. 7). In the example shown in FIG. 8A, the indicia 865 include a scale of millimeters from 10 to 40 along the transverse dimension of the sliding lateral member 815.

With continued reference to FIG. 8A, transferring the measurements to the device at step 220 may include moving the medical element guides 820 to positions on the wings of the sliding lateral member 815 such that a position indicator of each medical element guide 820 head coincides with a location in the scale of the indicia 865 that matches the lateral distance determined at step 215. In the example of FIG. 6, the lateral distance is determined to be 20 mm. Using this exemplary length measurement, at step 220 the user would move each medical element guide 820 along its wings of the sliding lateral member 815 until a position indicator on the medical element guide 820 coincides with a location corresponding to the number 20 in the scale of the indicia 865. In situations where the number of the lateral distance does not align exactly with one of the numbers of the indicia 865, the user may interpolate a position for the indicator between two numbers of the indicia 850 that best matches the lateral distance. After positioning the medical element guides 820 on the wings of the sliding lateral member 815 according to the lateral distance, the user may lock the medical element guides 820 relative to the sliding lateral member 815.

With continued reference to FIGS. 8A and 8B, in embodiments each of the medical element guides 820 includes a graduated needle guide 870 including plural needle guide slots 875 arranged at different predefined angles. The different predefined angles are within a range that is most likely to include the determined angle measurement of most patients. For example, the different predefined angles are within a range of 90 degrees to 140 degrees with a discrete one of the plural needle guide slots 875 arranged at increments of 10 degrees within this range. Each respective one of the plural needle guide slots 875 may be provided with indicia that indicates the angle of the respective one of the plural needle guide slots 875. Step 220 may include selecting one of the plural needle guide slots 875 based on the angle measurement determined at step 215. For example, for an angle measurement of 106.5 degrees, the user would select the one of the plural needle guide slots 875 that has an angle closest to 106.5 degrees. In an example in which the needle guide slots are arranged at a 10-degree increment between 90 degrees and 140 degrees, the user would select the 110 degrees angle guide slot for an angle measurement of 106.5 degrees.

Figure 8G:
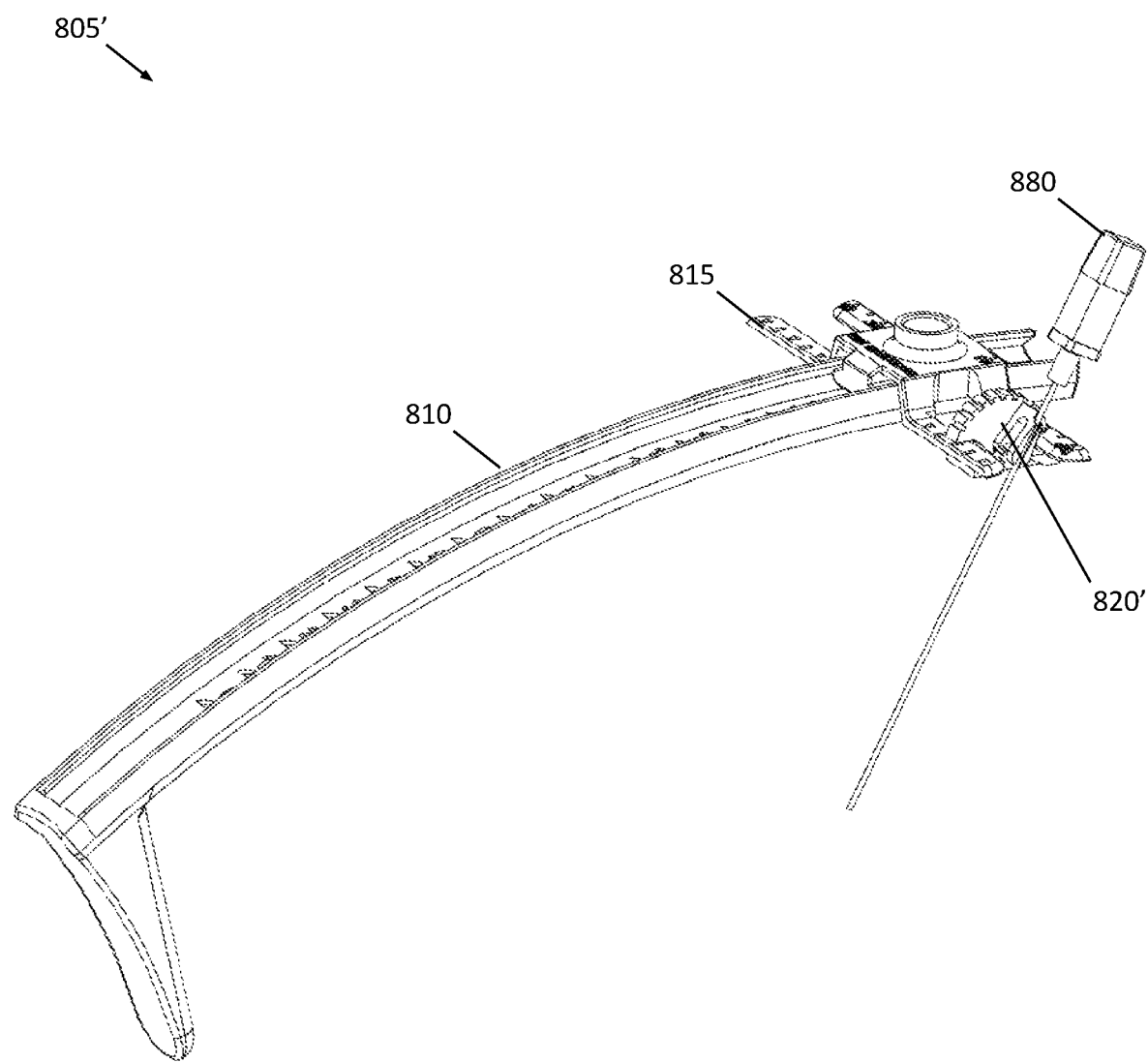
Figure 11A:
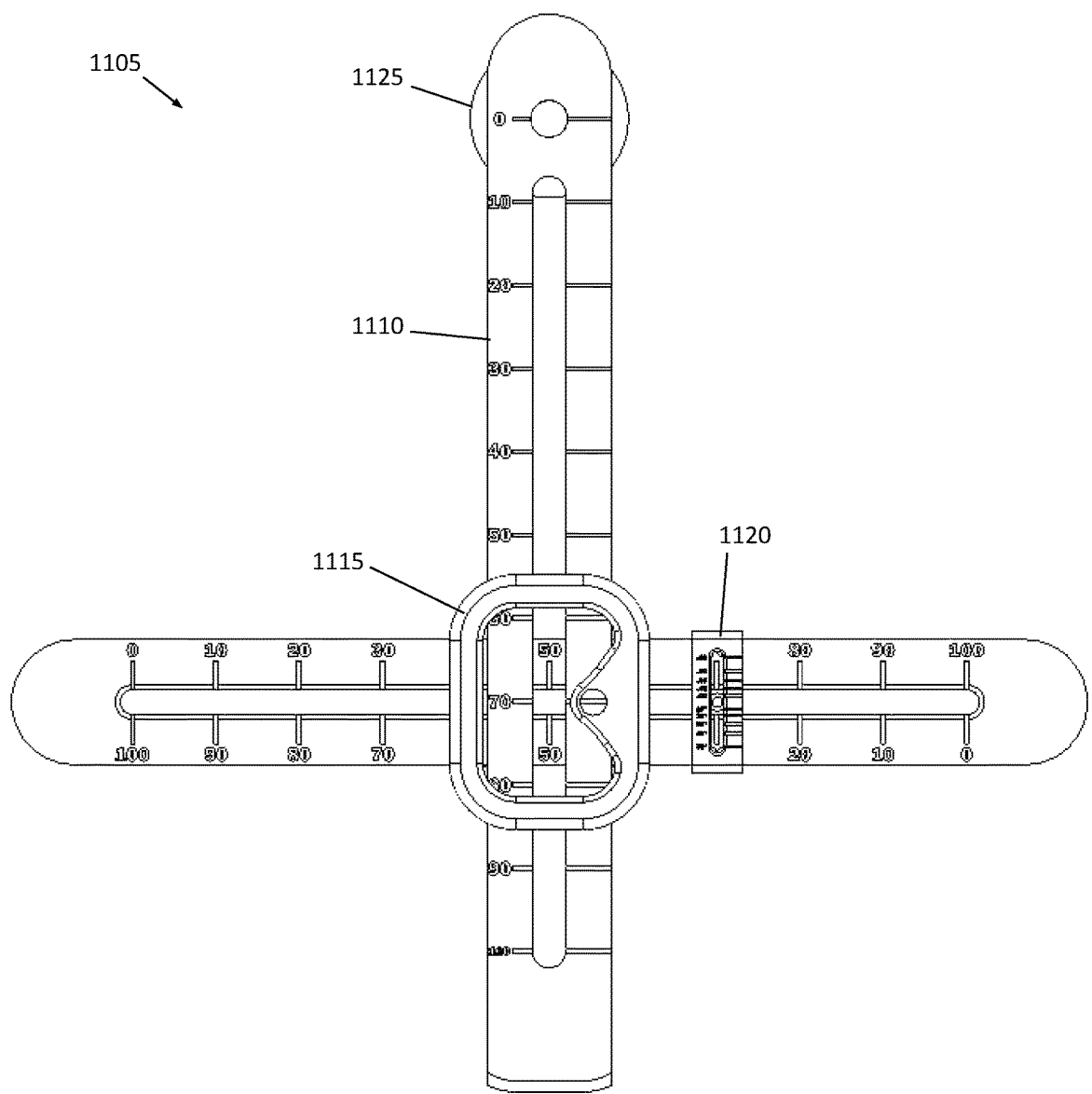
FIGS. 11A-G show an exemplary needle guide device.
Figure 11B:
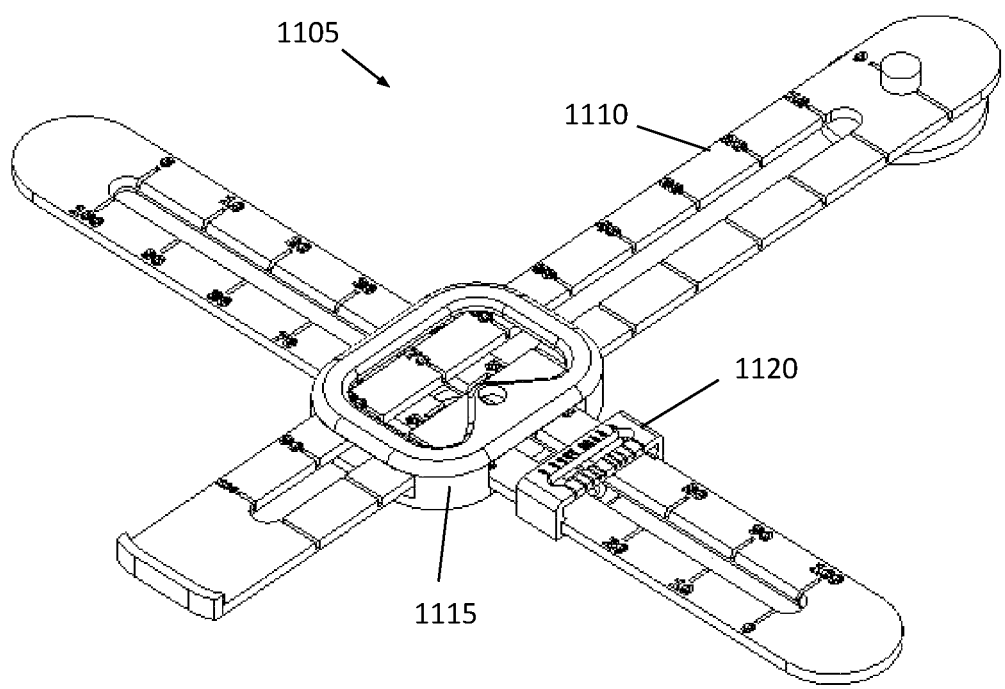
Figure 11C:
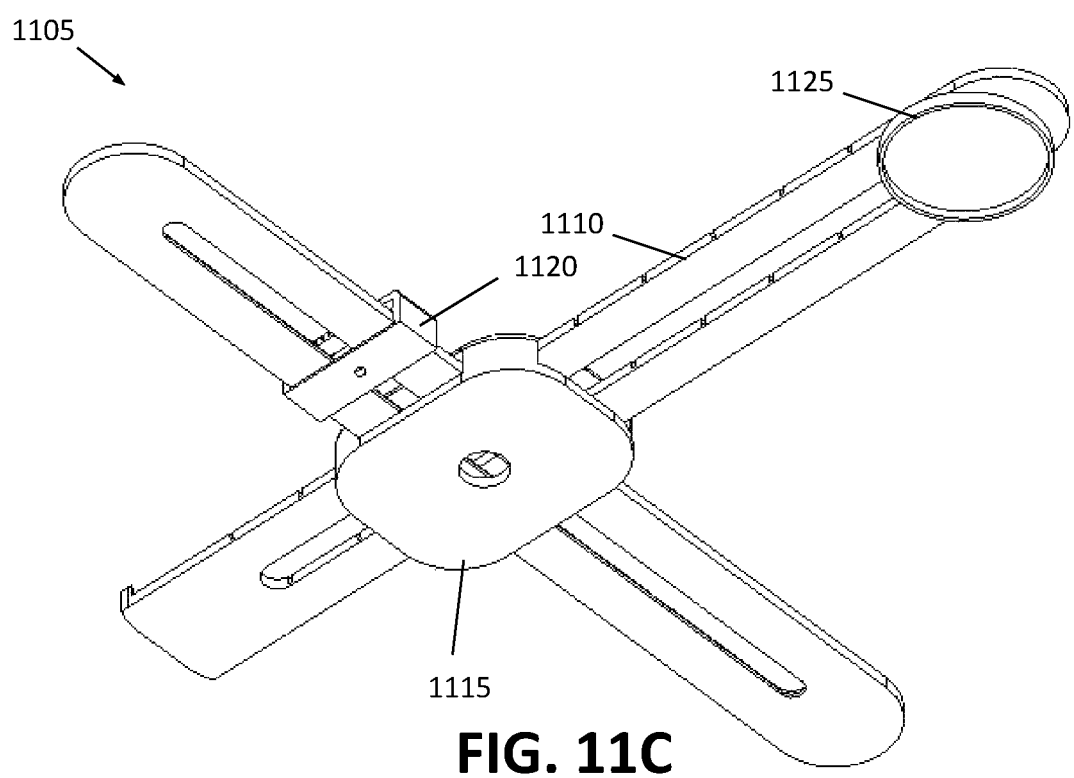
Figure 11D:
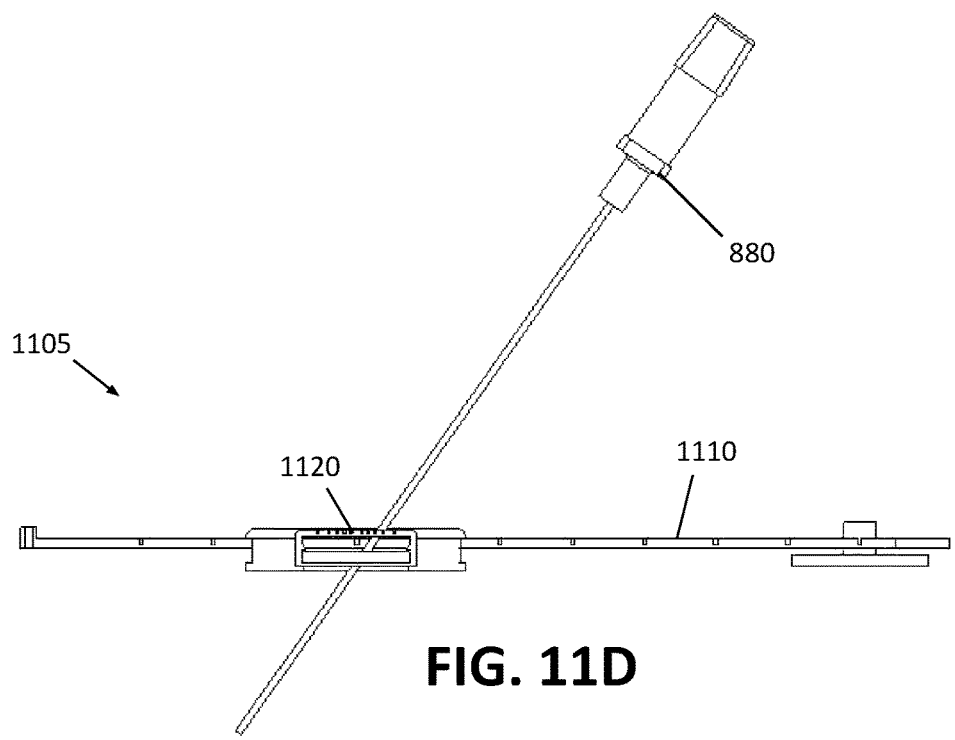
Figure 11E:
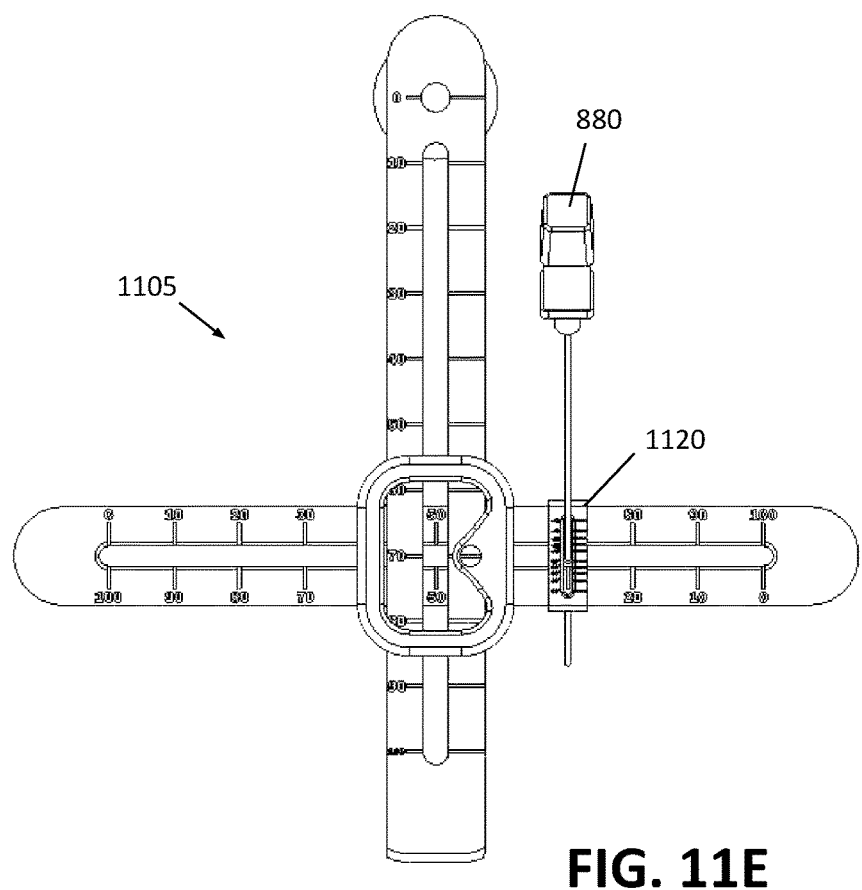
Figure 11F:
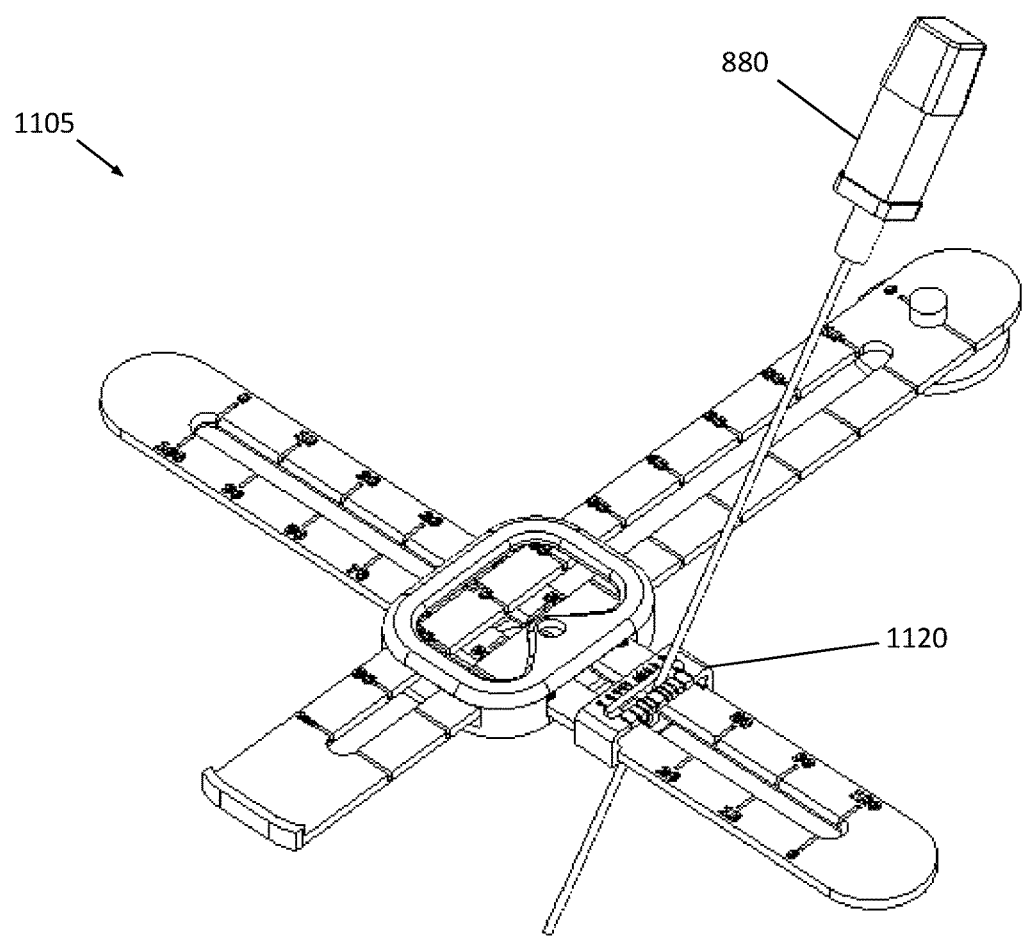

Other mechanisms for guiding the needle at selected angles may be utilized as an alternative to the guide slots 875. For example, FIG. 8G shows an exemplary embodiment of the device 805' in which each of the medical element guides 820' includes a single needle slot and the medical element guide 820' is rotatable around an axis that is parallel to the directions defined by 861 and 862 and perpendicular to the directions defined by 841 and 842 relative to the sliding lateral member 815 to plural different positions that correspond to different insertion angles of a needle into the patient. The plural different positions may correspond to different insertion angles in predefined increments of 10 degrees, for example. In this manner, the angle adjustment of the medical element guide 820' may function in the manner of an adjustable protractor that is affixed to the sliding lateral member 815. The rotation of the medical element guides 820' relative to the sliding lateral member 815 may be selectively locked and unlocked using a locking mechanism. The elements of the device 805' function in the same manner as those elements of the device 805 with the exception that the medical element guide 820' having a single needle guide that is rotatable to different angles and the medical element guide 820 having plural needle guides at different angles. The angle of the needle may also be guided by alternative mechanisms such as element 1120 shown in FIG. 11A. The increments of the needle guides described herein could be varied as suitable for the procedure being performed. For example, the guide angles could be positioned at angle increments ranging 5 to 20 degrees. In addition, the various guides disclosed herein may be sized to accommodate various size such as, for example, Gauge 20 and Gauge 19 needles.

In the manner described above, measurements determined at step 215 are transferred (e.g., by the user) to the device 805. In one example, the scales of the different indicia on the device 805 correspond to the scales of the different measurements determined at step 215. In another example, the measurements determined at step 215 are converted to values within the range of scales of the different indicia on the device 805 using predefined conversion formulas. In this manner, the application may output a set of numbers (e.g., the exact measurements or the converted values), and the user may adjust the device based on the numbers provided in this output.

FIGS. 8C, 8D, 8E, and 8F show views of the device 805 with a foramen needle 880 in one of the guide slots 875 of one of the medical element guides 820. As shown in FIGS. 8C-F, the guide slots are open on an outer end so that the medical element guide 820 may be moved away from the foramen needle 880 when the foramen needle 880 is inserted into the patient body. This permits adjusting the placement of the medical element (needle) angle or removal of the device 805 from the patient after a foramen needle 880 have been inserted using each of the medical element guides 820.

Figure 9:
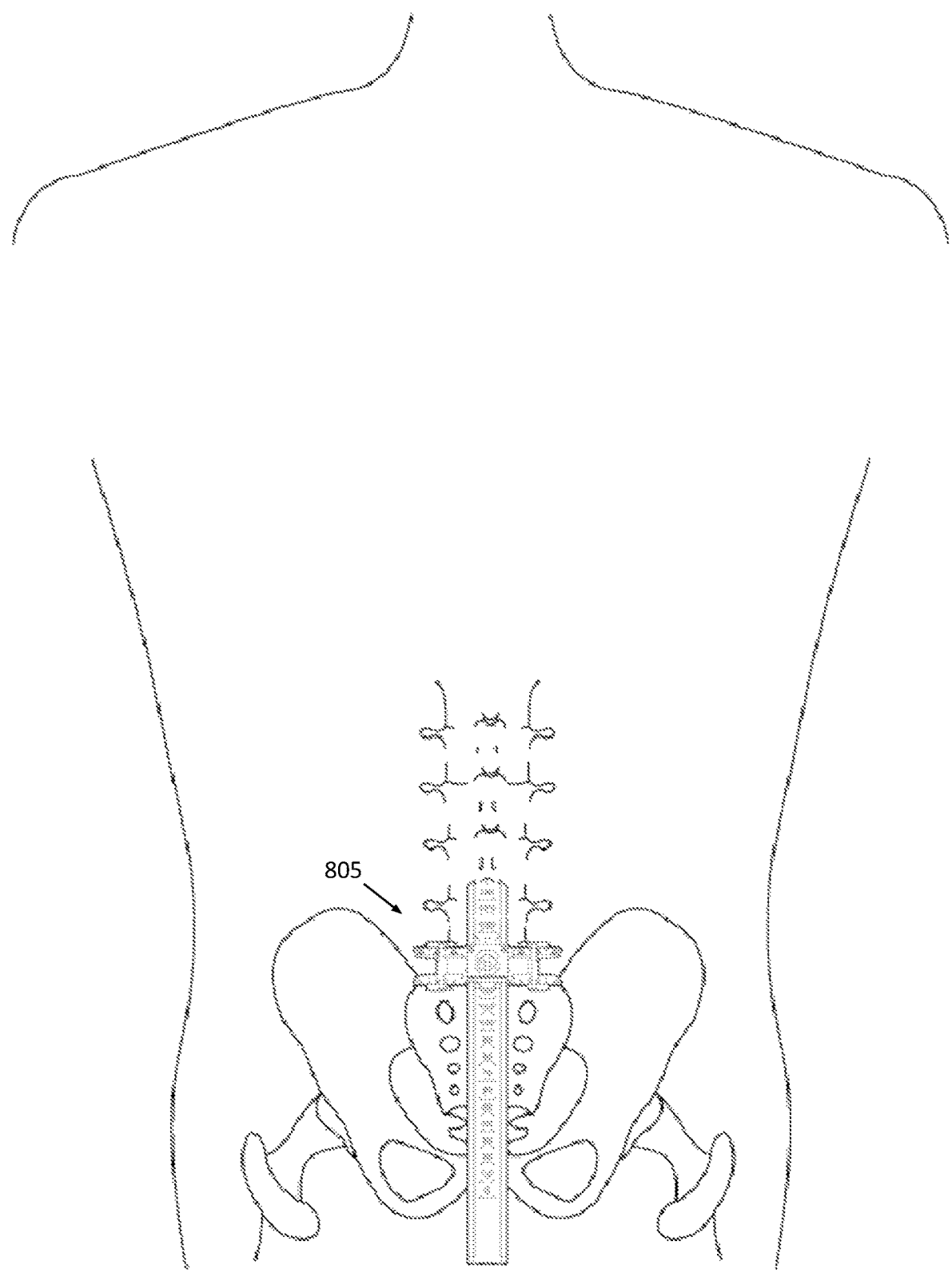
FIG. 9 shows an example of placing a needle guide device on a patient using a locating feature.

FIG. 9 shows an example of placing the device 805 on the patient using a locating feature. Step 225, described above, may include locating the device of the patient using a location feature. After transferring the measurements to the device 805 at step 220 (e.g., as described with respect to FIGS. 8A and 8B), the user places the device 805 on the patient, i.e., the same patient that was imaged at step 205. Placing the device 805 at step 220 includes positioning the device 805 on the outer surface of the skin of the patient who is in a prone position with the depending portion 825 of the device positioned adjacent to the coccyx of the patient and the elongated base 810 of the device 805 aligned with the spine of the patient.

Figure 10:
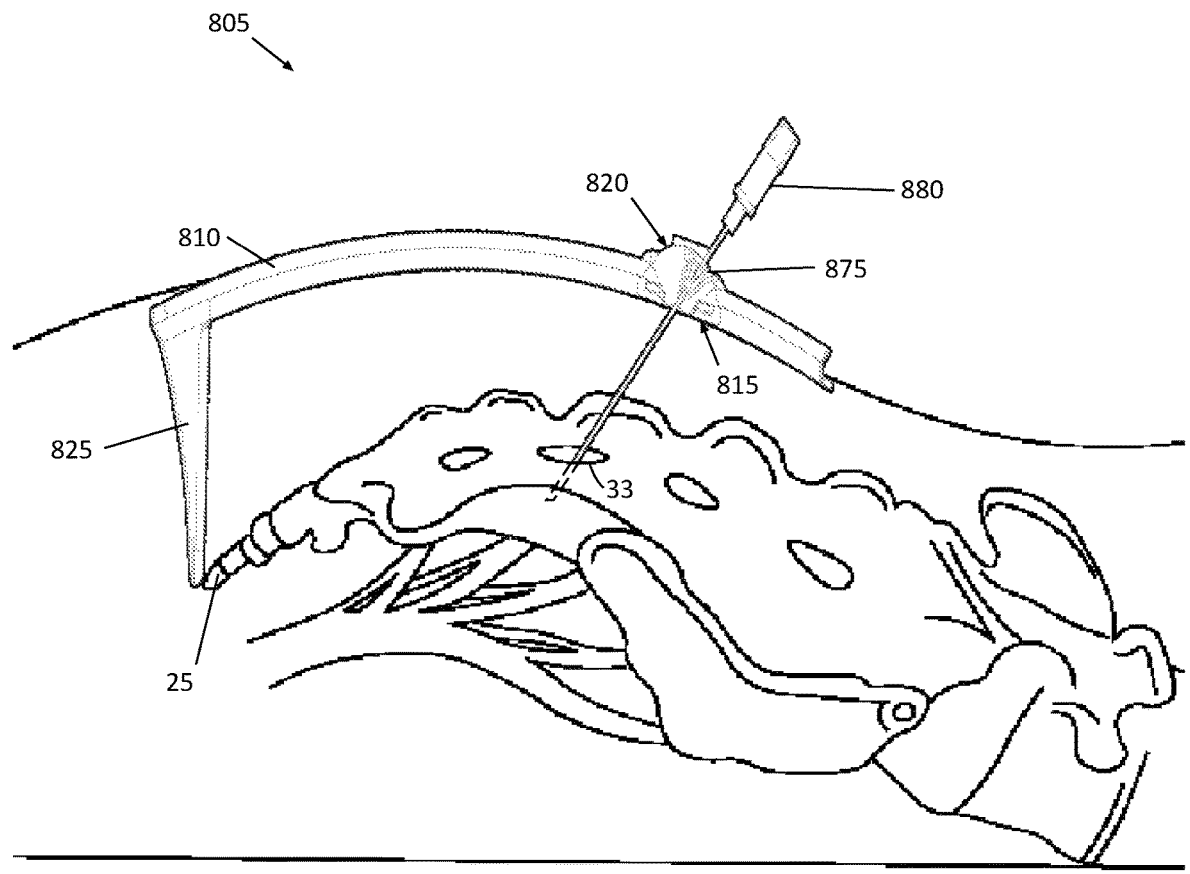
FIG. 10 shows an example of guiding a medical element into the patient using a needle guide device.

FIG. 10 shows an example of guiding a medical element into the patient using the device 805. FIG. 10 shows the device 805 placed on the patient as described with respect to step 225 and FIG. 9, e.g., with the device 805 on the outer surface of the skin of the patient who is in a prone position, with the depending portion 825 of the device positioned adjacent to the coccyx 25 of the patient, and the elongated base 810 of the device 805 aligned with the spine of the patient. After transferring the measurements to the device 805 at step 220 and then placing the device 805 on the patient at step 825, step 230 includes using the device 805 placed on the patient as a guide for inserting a needle (e.g., a foramen needle 880) into the patient. The user starts the foramen needle 880 in the selected one of the needle guide slots 875 (e.g., selected based on the angle measurement) and inserts the foramen needle 880 through this selected guide slot and into the patient. The location and angle of the needle insertion into the patient are defined by the device 805, which has been adjusted based on measurements determined from the location of the S3 foramen and other landmarks in this patient's imaging. Due to this, the location and angle of the needle insertion using the inventive method and device has a much higher rate of success of accurately locating the S3 foramen 33 in the patient compared to conventional blind techniques.

The foramen needle 880 may be provided with indicia that indicate a depth of insertion of the needle into the patient. The user may insert the foramen needle into the patient using the depth of insertion indicia to determine when the tip of the foramen needle 880 is close to the nerve in the S3 foramen.

After inserting a respective foramen needle on either side of the patient in the manner described, the medical element guides 820 may be moved inward along the sliding lateral member 815 away from the respective foramen needle, such that the device 805 may be removed from the patient. After inserting the foramen needle in the patient in this manner, the PNE procedure may proceed in a conventional fashion. For example, portions of the foramen needle may be removed and remaining portions of the foramen needle still in the patient may be used to insert implantable device leads into the patient.

Figure 11G:
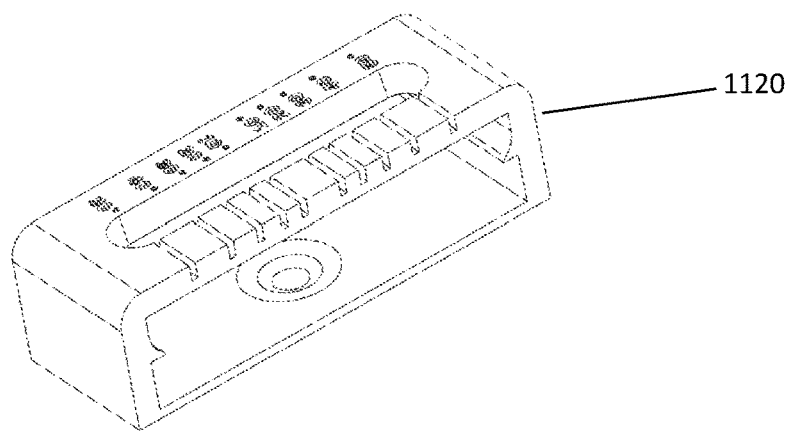
Figure 12:
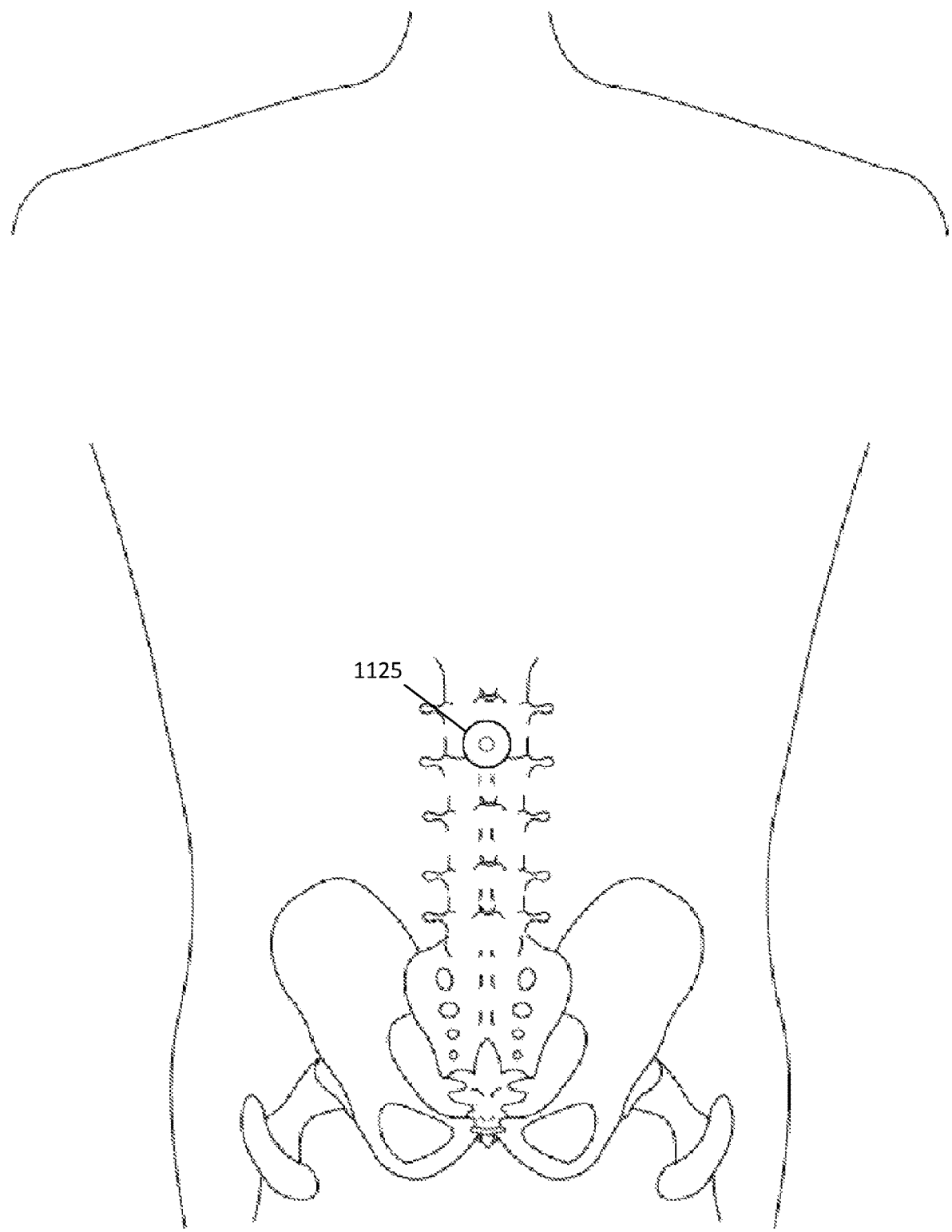
FIG. 12 shows an example of a locating element affixed to a patient.

FIGS. 11A-F show aspects of another example of a needle guide device 1105. The device 1105 includes an elongated base 1110, sliding lateral member 1115, and one or two medical element guides 1120, all of which operate in a similar manner as those similarly named elements described with respect to FIGS. 8A-F. The device 1105 includes a locating element 1125 that is connectable to the elongated base 1110. The locating element 1125 includes a disc or other shaped structure that is affixed to the patient during the imaging (e.g., step 205). The locating element 1125 may be affixed to the patient using adhesive or other methods. The locating element is affixed to the patient prior to imaging (e.g., at step 205) and remains fixed to the patient throughout needle insertion (e.g., at step 230). FIG. 12 shows an example of the locating element 1125 affixed to the patient. FIG. 11G shows an example of the medical element guide 1120.

The locating element 1125 includes a radiopaque portion that is visible in the imaging. The identifying points of interest (e.g., step 210) and processing the image for measurements (e.g., step 215) are performed based on the radiopaque portion of the locating element 1125 for the first point of interest and landmark rather than the tip of the coccyx as described at FIG. 6. In embodiments that utilize the device 1105, the application is programmed with geometric relationships that are based on the landmark coordinates of the locating element 1125 on the patient in the image, the coordinates of the S3 foramen in the image, and the predefined dimensions of the elongated base 1110. Using this information, the application uses the geometric relationships to determine a length measurement, an angle measurement, and a depth measurement, e.g., in a manner similar to that described above but with different use defined points of interest and with different geometric relationships.

After determining the length measurement, an angle measurement, and a depth measurement for the device 1105, the user transfers these measurements to the device 1105 (e.g., at step 220). This may be performed in a manner similar to the description of step 220 with device 805. For example, the application may output numbers that corresponds to measurements along the degrees of freedom of the device 1105, and the user may adjust the positions of the elements of the device 1105 based on these numbers. For example, the application may output a first number that is based on the determined length measurement, and the user may adjust the position of the sliding lateral member 1115 along the elongated base 1110 based on this number and based on indicia on the elongated base 1110.

Figure 13:
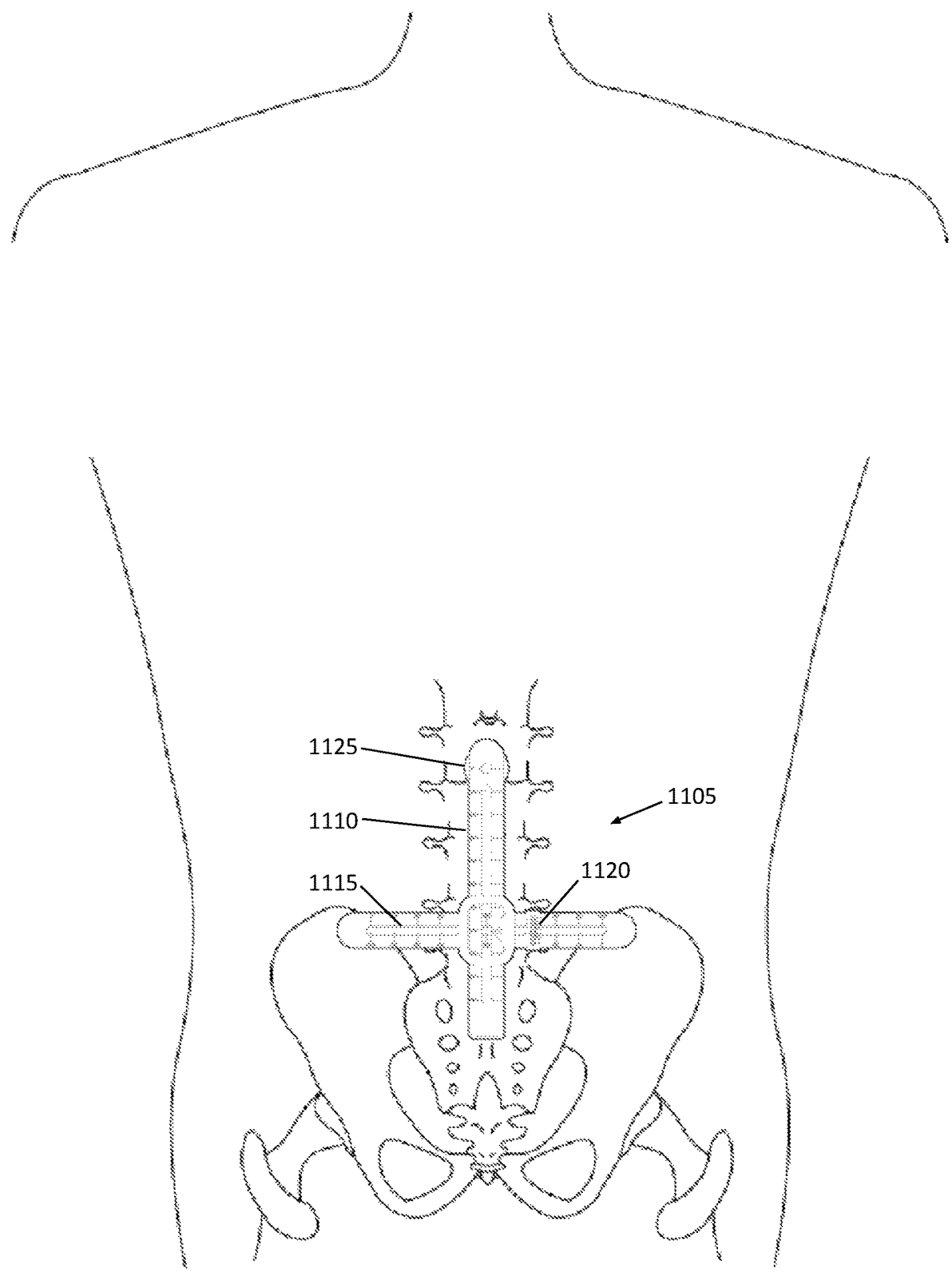
FIG. 13 shows an example of a locating element affixed to a patient and a needle guide device placed on the patient's back and connected to the locating element.

After adjusting the device 1105 based on the determined measurements, the user places the device on the patient using the locating feature. In this embodiment, the locating feature includes the locating element 1125. The elongated base 1110 is configured to connect to the locating element 1125, e.g., via snap fit or other connection mechanism. A portion of the elongated base 1110 that connects to the locating element 1125 may include a locating feature of the device and the locating element 1125 includes a landmark on the patient. Step 225 may include placing the device 1105 on the patient's back while the patient is in a prone position, connecting the elongated base 1110 to the locating element 1125 that is already affixed to the patient's back, and aligning the elongated base with the spine of the patient. FIG. 13 shows an example of the locating element 1125 affixed to the patient and the device 1105 placed on the patient's back and connected to the locating element 1125.

Figure 14:
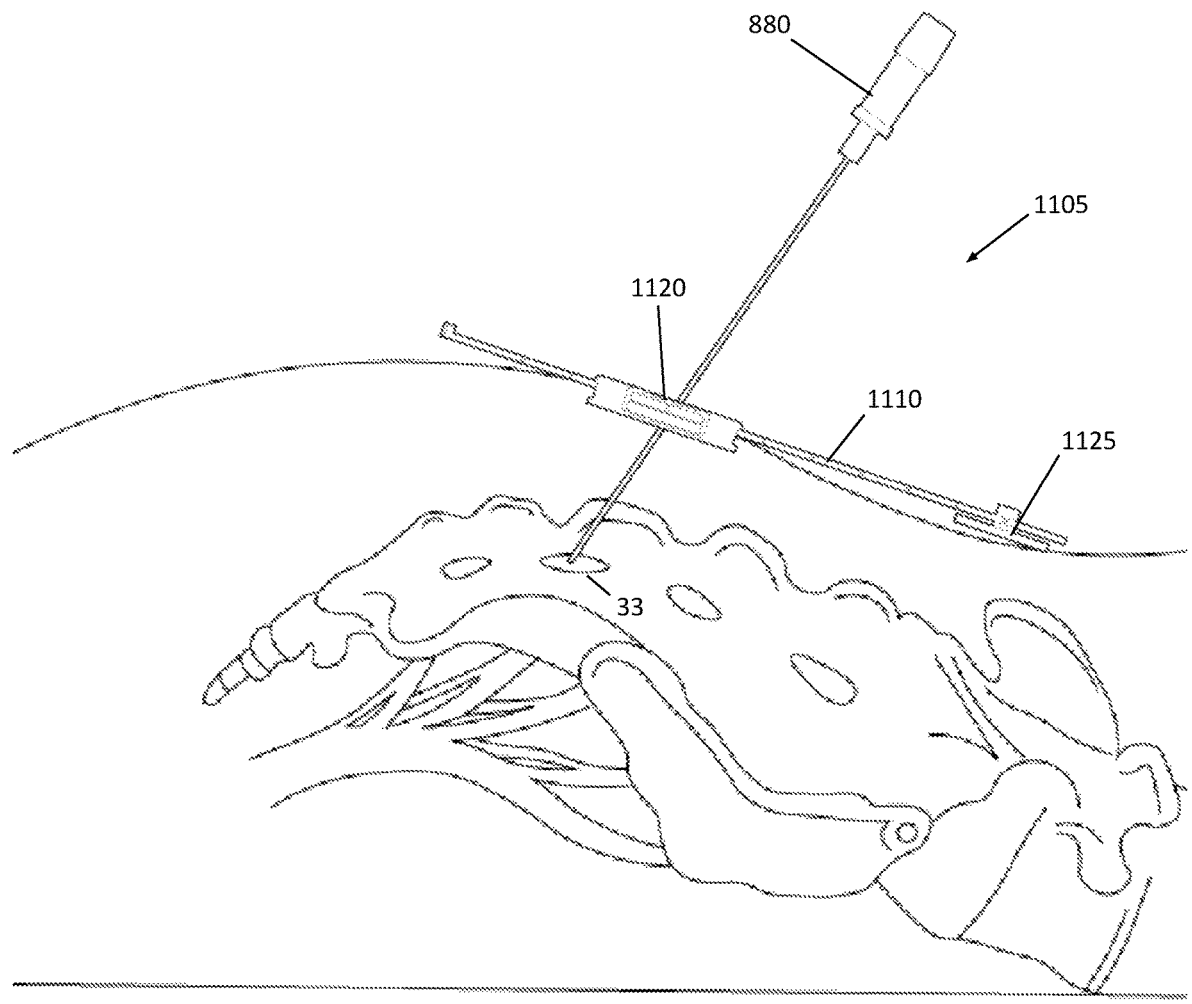
FIG. 14 shows an example of needle insertion using the needle guide device of FIGS. 11A-F.

After placing the device 1105 on the patient, the user utilizes the device 1105 as a guide for inserting a needle into the patient. Step 230 includes the user using the device 1105 as a guide for inserting a foramen needle 880 into the patient. As shown in FIG. 11G, the medical element guide 1120 may include an element that defines an aperture and plural angles that the user can select based on the determined angle measurement. The user puts the tip of the needle at the aperture at a base of the medical element guide 1120 and aligns the foramen needle 880 with a selected one of plural angles on the medical element guide 1120 based on the determined angle measurement. The needle arranged in this manner is then inserted into the patient. FIG. 14 shows an example of needle insertion using the device 1105 as a guide. The location and angle of the needle insertion into the patient are defined by the device 1105, which has been adjusted based on measurements determined from the location of the S3 foramen and other landmarks in this patient's imaging. Due to this, the location and angle of the needle insertion using the inventive method and device has a much higher rate of success of accurately locating the S3 foramen in the patient compared to conventional blind techniques.

The devices described herein (e.g., devices 805/805'/1105) are not limited to use with a foramen needle (such as foramen needle 880) and may be used to guide the insertion of other types of medical elements into the patient. For example, the devices may be used to guide insertion of medical elements including but not limited to foramen needles, other types of needles, leads, instruments, scopes, etc.

Figure 15:
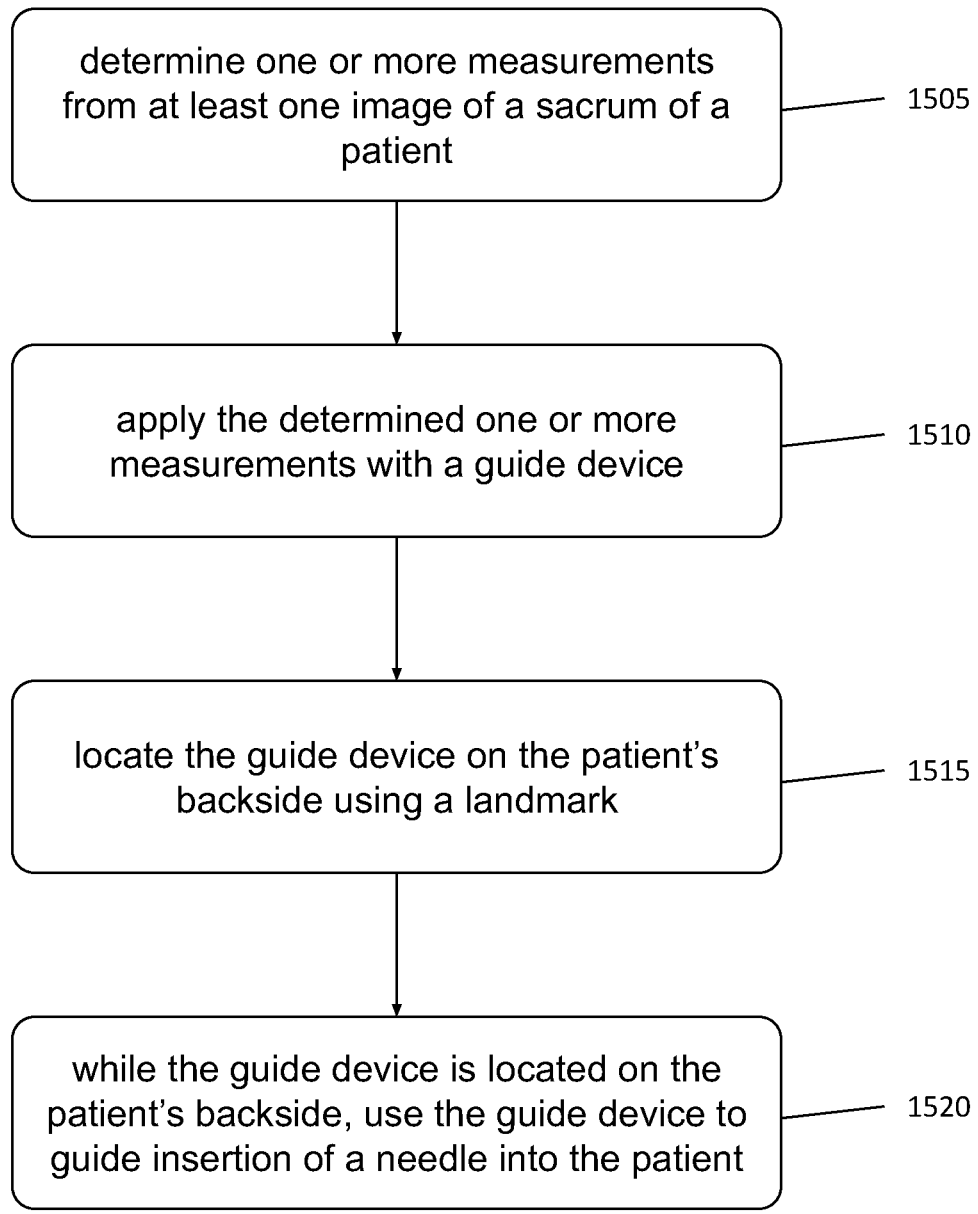
FIG. 15 shows a flowchart of an exemplary method for locating and placing a needle into a patient for the purpose of placing a PNE lead.

FIG. 15 shows a flowchart of an exemplary method for locating and placement of a medical element. Step 1505 includes determining one or more measurements from at least one image of a sacrum of a patient. In a non-limiting example, the measurements are determined in the manner described at FIGS. 6 and/or 7. Step 1510 includes applying the determined one or more measurements with a guide device. In a non-limiting example, the applying step includes making one or more adjustments to the device 805/805'/1105 based on the determined one or more measurements in the manner described herein. Step 1515 includes locating the guide device on the patient's backside using a landmark. In non-limiting examples, the locating may be performed in the manner described at FIGS. 9-10 or FIGS. 12-14. In a non-limiting example, the landmark includes the patient's coccyx. In a non-limiting example, the landmark includes a locating element affixed to the patient. Step 1520 includes, while the guide device is located on the patient's backside, using the guide device to guide insertion of a needle into the patient. In non-limiting examples, the guiding insertion may be performed in the manner described at FIG. 10 or FIG. 14.

As will be understood from the present disclosure an exemplary method is disclosed that includes the steps of: determining one or more measurements from at least one image of a sacrum of a patient; applying the determined one or more measurements with a guide device; locating the guide device on the patient's backside using a landmark; and while the guide device is located on the patient's backside, using the guide device to guide insertion of a medical element into the patient.

In embodiments of the method, the guide device may be adjustable and applying the determined one or more measurements with the guide device may include adjusting the guide device based on the one or more measurements.

In embodiments of the method, the landmark includes the patient's coccyx.

In embodiments of the method, the landmark includes a locating element affixed to the patient.

In embodiments of the method, the at least one image includes an image of a pelvis of the patient in a lateral plane. In embodiments of the method, the at least one image includes an image of the pelvis of the patient in a posterior-anterior plane or an anterior posterior plane. In embodiments of the method, the at least one image includes an X-ray or a CT scan.

In embodiments of the method, the one or more measurements are determined based on user input defining points of interest in the at least one image. In embodiments of the method, the points of interest in the image include a location of a foramen in the sacrum. In embodiments of the method, the one or more measurements are determined based on a predefined dimension of the guide device.

In embodiments of the method, the guide device on the patient's backside defines a location and an angle of entry of the medical element into the patient's body.

In embodiments of the method, the medical element includes a needle.

In another disclosed embodiment, a device for guiding medical element insertion may include: an elongated base with a locating feature that references a landmark on a patient; a head that is translatable along the elongated base in a first direction; and a medical element guide that is translatable along the head in a second direction perpendicular to the first direction, wherein the medical element guide is configured to identify the entry location and angle of insertion of a medical element into the patient.

In embodiments of the device, the elongated base is arced with a radius of curvature.

In embodiments of the device, the locating feature depends downward from the elongated base; the landmark includes the patient's coccyx; and the locating feature is configured to be located against the patient's coccyx when the device is placed on the patient's backside.

In embodiments of the device, the landmark includes a locating element affixed to the patient; and the locating feature includes a portion of the device that connects to the locating element. In embodiments of the device, the locating element includes a radiopaque marker.

In embodiments of the device, the medical element includes a needle.

In embodiments of the device, the entry location and angle of the medical element into the patient are configured to cause the medical element to pass through a selected foramen in the patient's sacrum.

In embodiments of the device, the medical element guide defines plural different angles for the angle of insertion of the medical element into the patient. In embodiments of the device, the plural different angles include plural different predefined angles that are defined by plural grooves in the medical element guide. In embodiments of the device, the plural different angles are defined by plural rotational locations of the medical element guide relative to the head.

As will be understood from the present disclosure a computer program product may be provided that includes one or more computer readable storage media having program instructions collectively stored on the one or more computer readable storage media, where the program instructions are executable to: receive at least one image of a sacrum of a patient; display the image; receive user input defining points of interest in the displayed image; determine one or more measurements for a medical element guide based on the points of interest and a predefined dimension of the medical element guide; and output the determined one or more measurements to a user.

In embodiments of the computer program product the points of interest include: a first point at a tip of the patient's coccyx or other landmark; and a second point at a foramen in the patient's sacrum. In embodiments of the computer program product the points of interest further include: a third point at an intersection of a surface of the patient's skin and a first line extending from the first point; and a fourth point at an intersection of the surface of the patient's skin and a second line extending from the second point.

In embodiments of the computer program product the medical guide element is configured to define a location and angle of insertion of a medical element into the patient while the medical guide element is located on the patient's backside.

Additional embodiments may include manufacturing and/or using the device 805 or 1105 as described herein. Also, instructions for using the device 805 or 1105 as described herein may be provided. The instructions may be provided in print and/or in video.

A training platform may be provided for the disclosed method and device. The training platform is a software platform for doctors, sales reps, or any other person that needs to learn or practice the invented technique/method. The software platform allows users to upload mock patients and go through the measurement process, e.g., at steps 210 and 215. The software may be configured to grade the user on the accuracy of their user inputs and offer suggestions and tip on how to improve user input. The platform may be used to train and certify users virtually. The platform administrator can deploy training modules and updates to train and update users on the best practices. The platform administrator can also collect data on user experience and interaction. The platform can provide educational animations for various processes and procedures. Future data collection may be employed in this platform of later processing and optimization.

A training model may also be provided. The training model is a physical model used to train doctors, sales reps, physician assistances, nurses, etc., using the methods and devices 805 and/or 1105. The training model allows users to practice placement of the sacral lead alone or in use with the virtual training platform. The training model includes the sacral bone structure as well as surrounding bone and tissue structure important to this procedure. The training model includes a soft tissue simulating structure where the opacity may be adjusted to control internal visualization allowing users to block or see within the model. The training model includes targets that may be contacted or "hit" to confirm proper placement of the leads. When a target is hit a signal may be produced to confirm the proper placement. Additionally, the model anatomy may be adjusted to different levels to practice on different anatomies. This may be achieved by changing bone placement to change the dimensions needed to place the stimulator. This may also be achieved with different physical models altogether to represent different case complexities and scenarios.

Additionally, an AI platform may be provided. The AI platform may be configured to collect X-ray, measurement, and lead placement data that is obtained from monitoring the software platform, the success rate of patients, etc., and to use this data to optimize the lead/needle placements. The data may be used to facilitate machine learning to automatically identify points of interest for needle placement and the resulting measurements used for employing a guide tool on a patient. This data may be used to predict and optimize placement of leads resulting in more efficient conversions from an external pulse generator (EPG) to an implantable pulse generator (IPG).

An application (e.g., software) as described herein may include computing code stored on a computer readable storage medium and executed by processing circuitry of a computing device (e.g., computing device 700) to perform the functions described herein. The computing code may include routines, programs, objects, components, logic, data structures, and so on that perform particular tasks or implement particular data types that the code uses to carry out the functions of embodiments described herein. The application may be stored on a portable device (e.g., a USB drive). In addition, the application may include processing capability for handling the image files (e.g., DICOM files). Alternatively, the application may be configured to operate cooperatively from image processing software.

It is noted that the foregoing examples have been provided merely for the purpose of explanation and are in no way to be construed as limiting of implementations of the present invention. While aspects of the present invention have been described with reference to an exemplary embodiment, it is understood that the words which have been used herein are words of description and illustration, rather than words of limitation. Changes may be made, within the purview of the appended claims, as presently stated and as amended, without departing from the scope and spirit of the present disclosure in its aspects. Although implementations of the present invention have been described herein with reference to particular means, materials and embodiments, implementations disclosed herein are not intended to be limited to the particulars disclosed herein; rather, implementations of the present invention extend to all functionally equivalent structures, methods and uses, such as are within the scope of the appended claims.

What is claimed is:

1. An apparatus for guiding insertion of a needle into a patient receiving sacral nerve stimulation therapy, the apparatus comprising:
   an elongated base having a first set of indicia, configured to extend longitudinally along the back of the patient, wherein the base includes a depending portion extending downwards and configured to lay adjacent to and be pressed against the coccyx of the patient;

a lateral member slidably attached to the elongate base, wherein the lateral member includes a second set of indicia; and an element guide mounted to the lateral member configured to aid the insertion of the needle into the patient at a predetermined angle at the target location.

2. The apparatus of claim 1, further including an adjustable needle guide attached to the element guide.

3. The apparatus of claim 1, wherein the first set of indicia corresponds to a distance cephalad along the elongate base from an end of the coccyx.

4. The apparatus of claim 3, wherein the second set of indicia corresponds to a distance laterally away from the patient's spine.

5. The apparatus of claim 1, further comprising a radiopaque locating element configured to be selectively attached to the elongated base.

6. The apparatus of claim 5, wherein the first set of indicia corresponds to a distance relative to the locating element.

7. An apparatus for guiding insertion of a needle for sacral nerve stimulation therapy into a patient, the apparatus comprising:

an elongate base, having a first set of indicia configured to extend longitudinally along the back of the patient, wherein the base includes a depending portion extending downwards and configured to lay adjacent to and be pressed against the coccyx of the patient;

a lateral member, having a second set of indicia; wherein the lateral member is slidably attached to the elongate base;

a guide body slidably attached to the lateral member, wherein the guide body is configured to move in a direction perpendicular to the elongate base; and wherein the guide body includes an angled guide configured to guide the needle to a target location on the patient at a predetermined angle.

8. The apparatus of claim 7, the guide body includes a plurality of grooves configured to guide the needle.

9. The apparatus of claim 8, wherein the plurality of grooves is disposed in a fanned pattern.

10. The apparatus of claim 7, wherein the guide body further includes an aperture located on the base of the guide body and a third set of indicia disposed along a length of a slot on a top surface of the guide body.

11. The apparatus of claim 7, further comprising a radiopaque locating element configured to be selectively attached to the elongated base.

12. The apparatus of claim 11, wherein the first set of indicia corresponds to a distance relative to the locating element.

13. The apparatus of claim 7, wherein the first set of indicia correspond to a distance cephalad along the elongate base relative to a vertical reference line extending from an end of the coccyx to the elongate base.

14. The apparatus of claim 13, wherein the predetermined angle is measured relative to a line tangent to an arc length of the apparatus.

15. An apparatus for guiding insertion of a needle for sacral nerve stimulation therapy into a patient, the apparatus comprising:

an elongate base, having a first set of indicia configured to extend longitudinally along the back of the patient, wherein the base includes a depending portion extending downwards and configured to lay adjacent to and be pressed against the coccyx of the patient;

a lateral member, having a second set of indicia; wherein the lateral member is slidably attached to the elongate base;

a guide body attached to the lateral member; and wherein the guide body includes a plurality of angled openings configured to guide the needle to a target location on the patient at a predetermined angle.

16. The apparatus of claim 15, wherein each of the plurality of angled openings are configured as slots in the guide body.

17. The apparatus of claim 16, wherein at least two of the plurality of slots guide the needle to the same target location.

18. The apparatus of claim 17, wherein each of the plurality of slots extend at a predetermined angle relative to a line tangent to an arc length of the apparatus.

19. The apparatus of claim 15, wherein at least one of the plurality of angled openings is positioned on a opposite side of the elongate base from another one of the plurality of angled openings.

20. The apparatus of claim 19, wherein each of the plurality of angled openings are configured as slots in the guide body.

21. The apparatus of claim 15, wherein the first set of indicia correspond to a distance cephalad along the elongate base relative to a vertical reference line extending from an end of the coccyx to the elongate base.

* * * * *